(12) United States Patent
Wondka et al.

(10) Patent No.: US 8,939,152 B2
(45) Date of Patent: Jan. 27, 2015

(54) METHODS, SYSTEMS AND DEVICES FOR HUMIDIFYING A RESPIRATORY TRACT

(75) Inventors: Anthony D. Wondka, Thousand Oaks, CA (US); Joseph Cipollone, Laguna Niguel, CA (US); George A. Kassanis, San Francisco, CA (US); Todd W. Allum, Livermore, CA (US); Enrico Brambilla, Irvine, CA (US)

(73) Assignee: Breathe Technologies, Inc., Irvine, CA (US)

( * ) Notice: Subject to any disclaimer, the term of this patent is extended or adjusted under 35 U.S.C. 154(b) by 234 days.

(21) Appl. No.: 13/251,070

(22) Filed: Sep. 30, 2011

(65) Prior Publication Data
US 2012/0138050 A1    Jun. 7, 2012

Related U.S. Application Data

(60) Provisional application No. 61/388,528, filed on Sep. 30, 2010.

(51) Int. Cl.
*A61M 16/06* (2006.01)
*A62B 18/02* (2006.01)
(Continued)

(52) U.S. Cl.
CPC .............. *A61M 16/16* (2013.01); *A61M 11/005* (2013.01); *A61M 16/0666* (2013.01);
(Continued)

(58) Field of Classification Search
CPC ...................... A61M 16/0666; A61M 16/0672; A61M 16/0677; A61M 16/0808; A61M 16/1045; A61M 16/16; A61M 15/08; A62B 23/06; A62B 9/003; A62B 9/06

USPC ............ 128/204.18, 204.21, 206.21–206.22, 128/206.28, 207.13, 207.18
See application file for complete search history.

(56) References Cited

U.S. PATENT DOCUMENTS

| 50,641 A | 10/1865 | Stone |
| 428,592 A | 5/1890 | Chapman |

(Continued)

FOREIGN PATENT DOCUMENTS

| DE | 19626924 | 1/1998 |
| DE | 29902267 U1 | 7/1999 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Valerie L Skorupa
(74) *Attorney, Agent, or Firm* — Stetina Brunda Garred & Brucker

(57) ABSTRACT

Systems and methods are provided for humidifying ventilation gas. Systems and methods may include a nasal interface apparatus for receiving ventilation gas from gas delivery tubing and for humidifying ventilation gas. The nasal interface apparatus may have one or more channels within the nasal interface to deliver gas from a gas delivery circuit to a patient's nose; one or more structures in fluid communication with the one or more channels to direct ventilation gas to the patient's nose; and a hygroscopic material within the nasal interface in the flow path of the ventilation gas.

20 Claims, 15 Drawing Sheets

(51) Int. Cl.
*A62B 23/06* (2006.01)
*A62B 7/10* (2006.01)
*A61M 16/16* (2006.01)
*A61M 11/00* (2006.01)
*A61M 16/10* (2006.01)
*A61M 11/04* (2006.01)
*A61M 16/12* (2006.01)
*A61M 16/00* (2006.01)
*A61M 16/08* (2006.01)
*A61M 16/04* (2006.01)
*A61M 11/02* (2006.01)
*A61M 11/06* (2006.01)

(52) U.S. Cl.
CPC ...... *A61M 16/1045* (2013.01); *A61M 16/1075* (2013.01); *A61M 11/042* (2014.02); *A61M 16/108* (2014.02); *A61M 16/1095* (2014.02); *A61M 16/127* (2014.02); *A61M 16/161* (2014.02); *A61M 16/0012* (2014.02); *A61M 16/0883* (2014.02); *A61M 16/0051* (2013.01); *A61M 16/0057* (2013.01); *A61M 16/04* (2013.01); *A61M 11/02* (2013.01); *A61M 11/06* (2013.01); *A61M 2016/0027* (2013.01); *A61M 2016/0033* (2013.01); *A61M 2205/3368* (2013.01); *A61M 2205/7527* (2013.01)
USPC ............. 128/207.18; 128/206.18; 128/207.13

(56) References Cited

U.S. PATENT DOCUMENTS

| | | | |
|---|---|---|---|
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Plá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,232,665 A | 11/1980 | Vaseen |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |

(56) References Cited

U.S. PATENT DOCUMENTS

| | | | |
|---|---|---|---|
| 4,686,974 | A | 8/1987 | Sato et al. |
| 4,686,975 | A | 8/1987 | Naimon et al. |
| 4,688,961 | A | 8/1987 | Shioda et al. |
| 4,705,034 | A | 11/1987 | Perkins |
| 4,744,356 | A | 5/1988 | Greenwood |
| 4,747,403 | A | 5/1988 | Gluck et al. |
| 4,753,233 | A | 6/1988 | Grimes |
| 4,773,411 | A | 9/1988 | Downs |
| 4,776,333 | A | 10/1988 | Miyamae |
| 4,782,832 | A | 11/1988 | Trimble et al. |
| 4,784,130 | A | 11/1988 | Kenyon et al. |
| 4,803,981 | A | 2/1989 | Vickery |
| 4,807,616 | A | 2/1989 | Adahan |
| 4,807,617 | A | 2/1989 | Nesti |
| 4,808,160 | A | 2/1989 | Timmons et al. |
| 4,813,431 | A | 3/1989 | Brown |
| 4,817,897 | A | 4/1989 | Kreusel |
| 4,818,320 | A | 4/1989 | Weichselbaum |
| 4,823,788 | A | 4/1989 | Smith et al. |
| 4,825,859 | A | 5/1989 | Lambert |
| 4,827,922 | A | 5/1989 | Champain et al. |
| 4,832,014 | A | 5/1989 | Perkins |
| 4,838,255 | A | 6/1989 | Lambert |
| 4,841,953 | A | 6/1989 | Dodrill |
| 4,848,333 | A | 7/1989 | Waite |
| 4,850,350 | A | 7/1989 | Jackson |
| 4,865,586 | A | 9/1989 | Hedberg |
| 4,869,718 | A | 9/1989 | Brader |
| 4,870,961 | A * | 10/1989 | Barnard .................. 128/202.27 |
| 4,899,740 | A | 2/1990 | Napolitano |
| 4,905,688 | A | 3/1990 | Vicenzi et al. |
| 4,915,103 | A | 4/1990 | Visveshwara et al. |
| 4,915,105 | A | 4/1990 | Lee |
| 4,919,128 | A | 4/1990 | Kopala et al. |
| 4,919,132 | A | 4/1990 | Miser |
| 4,938,212 | A | 7/1990 | Snook et al. |
| 4,944,310 | A | 7/1990 | Sullivan |
| 4,967,743 | A | 11/1990 | Lambert |
| 4,971,049 | A | 11/1990 | Rotariu et al. |
| 4,982,735 | A | 1/1991 | Yagata et al. |
| 4,986,269 | A | 1/1991 | Hakkinen |
| 4,989,599 | A | 2/1991 | Carter |
| 4,990,157 | A | 2/1991 | Roberts et al. |
| 5,000,175 | A | 3/1991 | Pue |
| 5,002,050 | A | 3/1991 | McGinnis |
| 5,005,570 | A | 4/1991 | Perkins |
| 5,018,519 | A | 5/1991 | Brown |
| 5,022,394 | A | 6/1991 | Chmielinski |
| 5,024,219 | A | 6/1991 | Dietz |
| 5,025,805 | A | 6/1991 | Nutter |
| 5,038,771 | A | 8/1991 | Dietz |
| 5,042,478 | A | 8/1991 | Kopala et al. |
| 5,046,491 | A | 9/1991 | Derrick |
| 5,046,492 | A | 9/1991 | Stackhouse et al. |
| 5,048,515 | A | 9/1991 | Sanso |
| 5,048,516 | A | 9/1991 | Soderberg |
| 5,052,400 | A | 10/1991 | Dietz |
| 5,054,484 | A | 10/1991 | Hebeler, Jr. |
| 5,058,580 | A | 10/1991 | Hazard |
| 5,074,299 | A | 12/1991 | Dietz |
| 5,076,267 | A | 12/1991 | Pasternack |
| 5,090,408 | A | 2/1992 | Spofford et al. |
| 5,097,827 | A | 3/1992 | Izumi |
| 5,099,836 | A | 3/1992 | Rowland et al. |
| 5,099,837 | A | 3/1992 | Russel, Sr. et al. |
| 5,101,820 | A | 4/1992 | Christopher |
| 5,103,815 | A | 4/1992 | Siegel et al. |
| 5,105,807 | A | 4/1992 | Kahn et al. |
| 5,107,830 | A | 4/1992 | Younes |
| 5,107,831 | A | 4/1992 | Halpern et al. |
| 5,113,857 | A | 5/1992 | Dickerman et al. |
| 5,117,818 | A | 6/1992 | Palfy |
| 5,117,819 | A | 6/1992 | Servidio et al. |
| 5,127,400 | A | 7/1992 | DeVries et al. |
| 5,134,995 | A | 8/1992 | Gruenke et al. |
| 5,134,996 | A | 8/1992 | Bell |
| 5,140,045 | A | 8/1992 | Askanazi et al. |
| 5,148,802 | A | 9/1992 | Sanders et al. |
| 5,161,525 | A | 11/1992 | Kimm et al. |
| 5,165,397 | A | 11/1992 | Arp |
| 5,181,509 | A | 1/1993 | Spofford et al. |
| 5,184,610 | A | 2/1993 | Marten et al. |
| 5,186,167 | A | 2/1993 | Kolobow |
| 5,193,532 | A | 3/1993 | Moa et al. |
| 5,193,533 | A | 3/1993 | Body et al. |
| 5,199,424 | A | 4/1993 | Sullivan et al. |
| 5,211,170 | A | 5/1993 | Press |
| 5,217,008 | A | 6/1993 | Lindholm |
| 5,233,978 | A | 8/1993 | Callaway |
| 5,233,979 | A | 8/1993 | Strickland |
| 5,239,994 | A | 8/1993 | Atkins |
| 5,239,995 | A | 8/1993 | Estes et al. |
| 5,243,972 | A | 9/1993 | Huang |
| 5,245,995 | A | 9/1993 | Sullivan et al. |
| 5,255,675 | A | 10/1993 | Kolobow |
| 5,258,027 | A | 11/1993 | Berghaus |
| 5,269,296 | A | 12/1993 | Landis |
| 5,271,388 | A | 12/1993 | Whitwam et al. |
| 5,271,391 | A | 12/1993 | Graves |
| 5,275,159 | A | 1/1994 | Griebel |
| 5,279,288 | A | 1/1994 | Christopher |
| 5,287,852 | A | 2/1994 | Arkinstall |
| 5,303,698 | A | 4/1994 | Tobia et al. |
| 5,303,700 | A | 4/1994 | Weismann et al. |
| 5,318,019 | A | 6/1994 | Celaya |
| 5,331,995 | A | 7/1994 | Westfall et al. |
| 5,335,656 | A | 8/1994 | Bowe et al. |
| 5,339,809 | A | 8/1994 | Beck, Jr. et al. |
| 5,349,946 | A | 9/1994 | McComb |
| 5,365,922 | A | 11/1994 | Raemer |
| 5,368,017 | A | 11/1994 | Sorenson et al. |
| 5,370,112 | A | 12/1994 | Perkins |
| 5,373,842 | A | 12/1994 | Olsson et al. |
| 5,375,593 | A | 12/1994 | Press |
| 5,388,575 | A | 2/1995 | Taube |
| 5,394,870 | A | 3/1995 | Johansson |
| 5,398,676 | A | 3/1995 | Press et al. |
| 5,398,682 | A | 3/1995 | Lynn |
| 5,400,778 | A | 3/1995 | Jonson et al. |
| 5,419,314 | A | 5/1995 | Christopher |
| 5,438,979 | A | 8/1995 | Johnson, Jr. et al. |
| 5,438,980 | A | 8/1995 | Phillips |
| 5,443,075 | A | 8/1995 | Holscher |
| 5,460,174 | A | 10/1995 | Chang |
| 5,460,613 | A | 10/1995 | Ulrich et al. |
| 5,474,062 | A | 12/1995 | DeVries et al. |
| 5,477,852 | A | 12/1995 | Landis et al. |
| 5,485,850 | A | 1/1996 | Dietz |
| 5,490,502 | A | 2/1996 | Rapoport et al. |
| 5,503,146 | A | 4/1996 | Froehlich et al. |
| 5,503,497 | A | 4/1996 | Dudley et al. |
| 5,507,282 | A | 4/1996 | Younes |
| 5,509,409 | A | 4/1996 | Weatherholt |
| 5,511,542 | A | 4/1996 | Hall |
| 5,513,628 | A | 5/1996 | Coles et al. |
| 5,513,631 | A | 5/1996 | McWilliams |
| 5,513,635 | A | 5/1996 | Bedi |
| 5,522,382 | A | 6/1996 | Sullivan et al. |
| 5,526,806 | A | 6/1996 | Sansoni |
| 5,529,060 | A | 6/1996 | Salmon et al. |
| 5,533,506 | A | 7/1996 | Wood |
| 5,535,738 | A | 7/1996 | Estes et al. |
| 5,537,997 | A | 7/1996 | Mechlenburg et al. |
| 5,538,002 | A | 7/1996 | Boussignac et al. |
| 5,542,415 | A | 8/1996 | Brody |
| 5,546,935 | A | 8/1996 | Champeau |
| 5,549,106 | A | 8/1996 | Gruenke et al. |
| 5,551,419 | A | 9/1996 | Froehlich et al. |
| 5,558,086 | A | 9/1996 | Smith et al. |
| 5,564,416 | A | 10/1996 | Jones |
| 5,575,282 | A | 11/1996 | Knoch et al. |
| 5,582,164 | A | 12/1996 | Sanders |
| 5,593,143 | A | 1/1997 | Ferrarin |
| 5,595,174 | A | 1/1997 | Gwaltney |

(56) References Cited

U.S. PATENT DOCUMENTS

| | | |
|---|---|---|
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,829,428 A * | 11/1998 | Walters et al. ........... 128/200.24 |
| 5,845,636 A | 12/1998 | Gruenke et al. |
| 5,865,173 A | 2/1999 | Froehlich |
| 5,865,174 A | 2/1999 | Kloeppel |
| 5,881,723 A | 3/1999 | Wallace et al. |
| 5,896,857 A | 4/1999 | Hely et al. |
| 5,904,648 A | 5/1999 | Arndt et al. |
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,927,400 A | 7/1999 | Bononi et al. |
| 5,928,189 A | 7/1999 | Phillips et al. |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,095,505 A | 8/2000 | Miller |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller, Jr. |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |

(56) References Cited

U.S. PATENT DOCUMENTS

| | | |
|---|---|---|
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B2 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |

(56) References Cited

U.S. PATENT DOCUMENTS

| | | |
|---|---|---|
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,428,902 B2 * | 9/2008 | Du et al. .................. 128/204.17 |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 * | 9/2011 | Christopher et al. .... 128/207.18 |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |

(56) References Cited

U.S. PATENT DOCUMENTS

| | | |
|---|---|---|
| 2004/0050387 A1 | 3/2004 | Younes |
| 2004/0074494 A1 | 4/2004 | Frater |
| 2004/0084046 A1* | 5/2004 | Halperin ............... 128/201.13 |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0028823 A1* | 2/2005 | Wood ..................... 128/207.18 |
| 2005/0033247 A1 | 2/2005 | Thompson |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0151624 A1* | 7/2006 | Grundler et al. ................ 237/67 |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunaratnam et al. |
| 2008/0092905 A1 | 4/2008 | Gunaratnam et al. |
| 2008/0092906 A1 | 4/2008 | Gunaratnam et al. |
| 2008/0099024 A1 | 5/2008 | Gunaratnam et al. |
| 2008/0099027 A1 | 5/2008 | Gunaratnam et al. |
| 2008/0105264 A1 | 5/2008 | Gunaratnam et al. |
| 2008/0110462 A1 | 5/2008 | Chekal et al. |
| 2008/0121230 A1 | 5/2008 | Cortez et al. |
| 2008/0134690 A1 | 6/2008 | Reid |
| 2008/0135044 A1 | 6/2008 | Freitag et al. |
| 2008/0142013 A1 | 6/2008 | Hallett et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020015 A1 | 1/2009 | Sermet et al. |
| 2009/0020121 A1 | 1/2009 | Bassin |
| 2009/0044808 A1 | 2/2009 | Guney et al. |
| 2009/0056708 A1 | 3/2009 | Stenzler et al. |

(56) References Cited

U.S. PATENT DOCUMENTS

| | | |
|---|---|---|
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0217929 A1* | 9/2009 | Kwok et al. ............ 128/204.18 |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0253995 A1* | 10/2009 | Lewis et al. .................. 600/538 |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0018534 A1* | 1/2010 | Veliss et al. ............. 128/206.24 |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162647 A1* | 7/2011 | Huby et al. ............... 128/203.14 |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | S63-57060 | 3/1998 |
| JP | 2002-204830 | 7/2002 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01/76655 | 10/2001 |
| WO | WO-02/62413 | 8/2002 |
| WO | WO-2004/009169 | 1/2004 |
| WO | WO-2005/014091 | 2/2005 |
| WO | WO-2005/018524 | 3/2005 |
| WO | WO-2006/138580 | 12/2006 |
| WO | WO-2007/035804 | 3/2007 |
| WO | 2007042765 | 4/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |

(56) References Cited

FOREIGN PATENT DOCUMENTS

| | | |
|---|---|---|
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO-2010/021556 | 2/2010 |
| WO | WO-2010/022363 | 2/2010 |
| WO | WO-2010/039989 | 4/2010 |
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO-2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO-2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.

In the U.S. Patent and Trademark Office, Examiner's Interview Summary in re: U.S. Appl. No. 10/771,803, dated Oct. 31, 2008, 4 pages.

In the U.S. Patent and Trademark Office, Notice of Allowance dated in re: U.S. Appl. No. 10/771,803, dated Oct. 20, 2008, 8 pages.

In the U.S. Patent and Trademark Office, Examiner's Interview Summary in re: U.S. Appl. No. 10/771,803, dated Nov. 2, 2007, 2 pages.

In the U.S. Patent and Trademark Office, Office Action in re: U.S. Appl. No. 10/771,803, dated Jun. 14, 2007, 12 pages.

In the U.S. Patent and Trademark Office, Restriction Requirement in re: U.S. Appl. No. 12/271,484, dated Feb. 9, 2011, 5 pages.

In the U.S. Patent and Trademark Office, Restriction Requirement in re: U.S. Appl. No. 12/754,437, dated Aug. 16, 2011, 5 pages.

In the U.S. Patent and Trademark Office, Non-Final Office Action dated in re: U.S. Appl. No. 10/567,746, dated Oct. 5, 2009, 9 pages.

In the U.S. Patent and Trademark Office, Notice of Allowance and Examiner's Interview Summary in re: U.S. Appl. No. 11/523,519, dated Jan. 16, 2009, 10 pages.

In the U.S. Patent and Trademark Office, Examiner's Interview Summary in re: U.S. Appl. No. 11/523,519, dated Jan. 13, 2009, 4 pages.

In the U.S. Patent and Trademark Office, Final Office Action in re: U.S. Appl. No. 11/523,519, dated Jul. 11, 2008, 13 pages.

In the U.S. Patent and Trademark Office, Examiner's Interview Summary in re: U.S. Appl. No. 11/523,519, dated Apr. 10, 2008, 3 pages.

In the U.S. Patent and Trademark Office, Final Office Action in re: U.S. Appl. No. 11/523,519, dated Nov. 26, 2007, 14 pages.

In the U.S. Patent and Trademark Office, Office Action in re: U.S. Appl. No. 11/523,519, dated Mar. 7, 2007, 11 pages.

In the U.S. Patent and Trademark Office, Restriction Requirement in re: U.S. Appl. No. 11/523,518, dated Dec. 30, 2009, 4 pages.

In the U.S. Patent and Trademark Office, Supplemental Notice of Allowance in re: U.S. Appl. No. 11/798,965, dated Aug. 21, 2009, 4 pages.

In the U.S. Patent and Trademark Office, Notice of Allowance in re: U.S. Appl. No. 11/798,965, dated Jul. 17, 2009, 5 pages.

In the U.S. Patent and Trademark Office, Final Office Action in re: U.S. Appl. No. 11/798,965, dated Apr. 9, 2009, 6 pages.

In the U.S. Patent and Trademark Office, Office Action in re: U.S. Appl. No. 11/798,965, dated Jul. 29, 2008, 12 pages.

In the U.S. Patent and Trademark Office, Office Action in re: U.S. Appl. No. 12/578,283, dated Oct. 19, 2011, 5 pages.

In the U.S. Patent and Trademark Office, Restriction/Election Requirement in re: U.S. Appl. No. 11/882,530, dated Apr. 27, 2011, 5 pages.

In the U.S. Patent and Trademark Office, Supplemental Notice of Allowance in re: U.S. Appl. No. 10/870,849, dated Jun. 16, 2009, 2 pages.

In the U.S. Patent and Trademark Office, Notice of Allowance in re: U.S. Appl. No. 10/870,849, dated Jun. 3, 2009, 4 pages.

In the U.S. Patent and Trademark Office, Notice of Allowance in re: U.S. Appl. No. 10/870,849, dated May 14, 2009, 8 pages.

In the U.S. Patent and Trademark Office, Restriction in re: U.S. Appl. No. 10/870,849, dated Nov. 16, 2007, 5 pages.

In the U.S. Patent and Trademark Office, Examiner's Interview Summary in re: U.S. Appl. No. 10/870,849, dated Jul. 27, 2007, 2 pages.

In the U.S. Patent and Trademark Office, Office Action in re: U.S. Appl. No. 10/870,849, dated Feb. 22, 2007, 13 pages.

In the U.S. Patent and Trademark Office, Restriction/Election Requirement in re: U.S. Appl. No. 12/493,677, dated Aug. 5, 2011, 5 pages.

In the U.S. Patent and Trademark Office, Restriction/Election Requirement in re: U.S. Appl. No. 12/153,423, dated Oct. 6, 2011, 8 pages.

In the U.S. Patent and Trademark Office, Notice of Allowance in re: U.S. Appl. No. 10/922,054, dated Feb. 12, 2008, 6 pages.

(56) References Cited

OTHER PUBLICATIONS

In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiner's Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, *Ex Parte Quayle* Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," *Chest*, 2005: 128(2), pp. 481-483.
Bach et al., "Intermittent Positive Pressure Ventilation via Nasal Access in the Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," Critical Care Medicine, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," *Crit Care Clin.*, 2007; 23(2): 201-22.
Bauer et al., "ADAM Nasal CPAP Circuit Adaptation: A Case Report," *Sleep*, 1991: 14(3), pp. 272-273.
Blanch, "Clinical Studies of Tracheal Gas Insufflation," *Resp. Care*, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," *Chest*, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," *Resp. Care*, 2001: 46(1), pp. 15-25.
Christopher, et al., "Transtracheal Oxygen Therapy for Refractory Hypoxemia," *JAMA*, 1986: 256(4), pp. 494-497.

Ciccolella et al.; "Administration of High-Flow, Vapor-phased, Humidified Nasal Cannula Air (HF-HNC) Decreases Work of Breathing (WOB) in Healthy Subjects During Exercise,"*AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.
Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.
Macinryre, "Long-Term Oxygen Therapy: Conference Summary," *Resp. Care*, 2000: 45(2), pp. 237-245.
Macintyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", Chest, 1988:94(6), pp. 1142-1147.
Nava et al., "Non-invasive ventilation," *Minerva Anestesiol.*, 2009: 75(1-2), pp. 31-36.

(56) References Cited

OTHER PUBLICATIONS

Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.
Rothe et al., "Near Fatal Complication of Transtracheal Oxygen Therapy with the SCOOP(R) System," *Pneumologie*, 1996: 50(10), pp. 700-702. (English Abstract provided.)
Rothfleisch et al., "Facilitation of fiberoptic nasotracheal intubation in a morbidly obese patient by simultaneous use of nasal CPAP," *Chest*, 1994, 106(1): 287-288.
Sanders et al., "CPAP Via Nasal Mask: A Treatment for Occlusive Sleep Apnea," *Chest*, 1983: 83(1), pp. 144-145.
Sinderby et al., "Neural control of mechanical ventilation in respiratory failure," *Nat. Med.*, 1999: 5(12), pp. 1433-1436.
Somfay et al., "Dose-Response Effect of Oxygen on Hyperinflation and Exercise Endurance in Nonhypoxaemic COPD Patients," *Eur. Resp. J.*, 2001: 18, pp. 77-84.
Sullivan et al., "Reversal of Obstructive Sleep Apnoea by Continuous Positive Airway Pressure Applied Through the Nares," *The Lancet*, 1981: 1(8225), pp. 862-865.
Sullivan, "Home treatment of obstructive sleep apnoea with continuous positive airway pressure applied through a nose-mask," *Bull Eur Physiopathol Respir.*, 1984: 20(1), pp. 49-54.
Tiep et al., "Pulsed nasal and transtracheal oxygen delivery," *Chest*, 1990: 97, pp. 364-368.
Tsuboi et al., "Ventilatory Support During Exercise in Patients With Pulmonary Tuberculosis Sequelae," *Chest*, 1997: 112(4), pp. 1000-1007.
*VHA/DOD Clinical Practice Guideline*, "Management of Chronic Obstructive Pulmonary Disease," Aug. 1999, Ver. 1.1a, Updated Nov. 1999.
Wijkstra et al., "Nocturnal non-invasive positive pressure ventilation for stable chronic obstructive pulmonary disease," *Cochrane Database Syst. Rev.*, 2002, 3: 1-22.

Yaeger et al., "Oxygen Therapy Using Pulse and Continuous Flow With a Transtracheal Catheter and a Nasal Cannula," *Chest*, 1994: 106, pp. 854-860.
Walsh, "McGraw Hill Pocket reference Machinists' and Metalworker' Pocket Reference," *New York McGraw-Hill*, 2000, pp. 3-67, submitting 3 pages.
International Preliminary Report and Written Opinion on Patentability for PCT/DE2004/001646, dated Jul. 3, 2006.
European patent Office Search Report issued Oct. 19, 2007 in co-pending EP 04762494.
International Search Report and Written Opinion for PCT/US04/26800 issued Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 issued Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.
International Search Report for PCT/US2011/047994, dated Dec. 13, 2011.
Australian Government, Patent Examination Report No. 1, Mar. 14, 2013, 5 Pages, Melbourne Australia.

\* cited by examiner

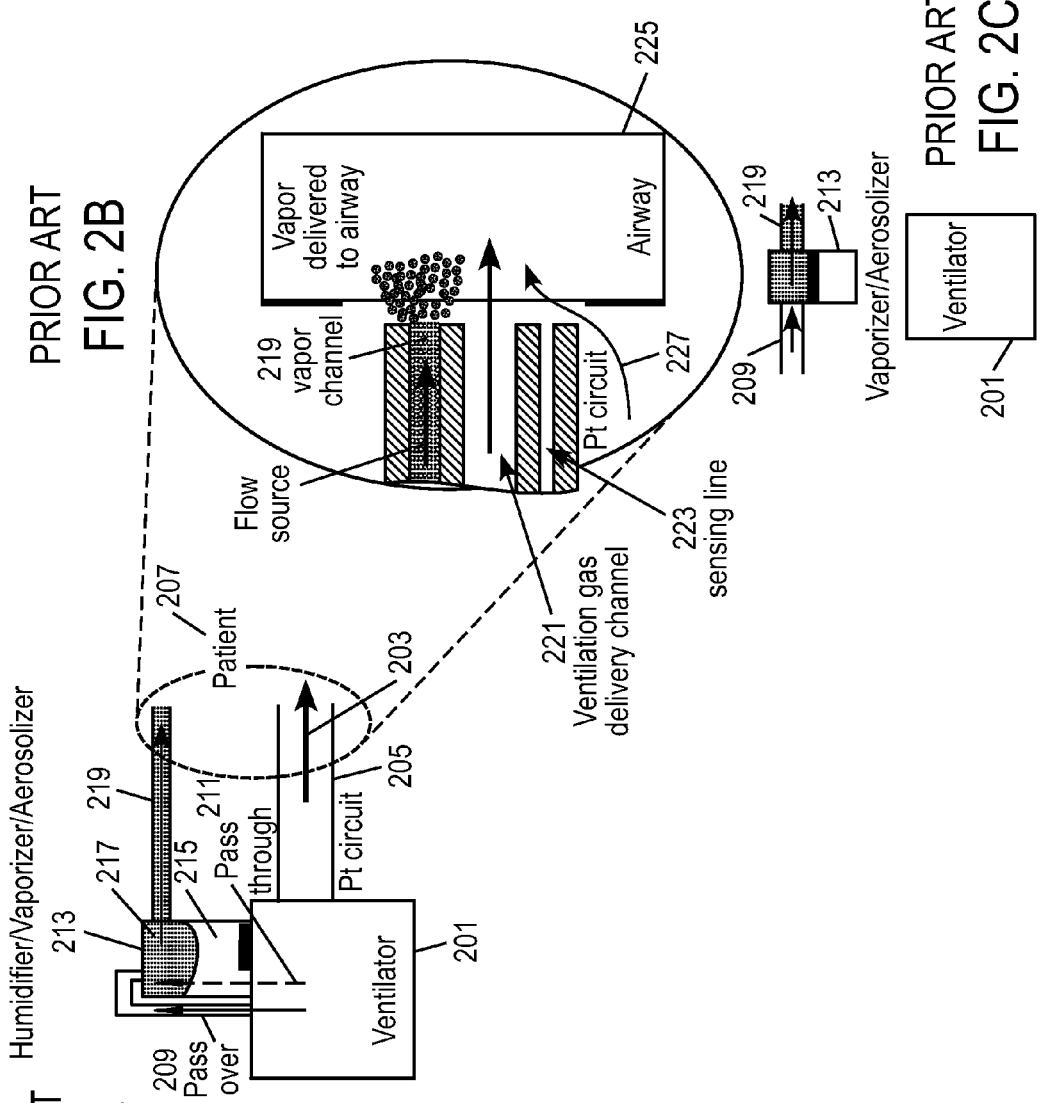

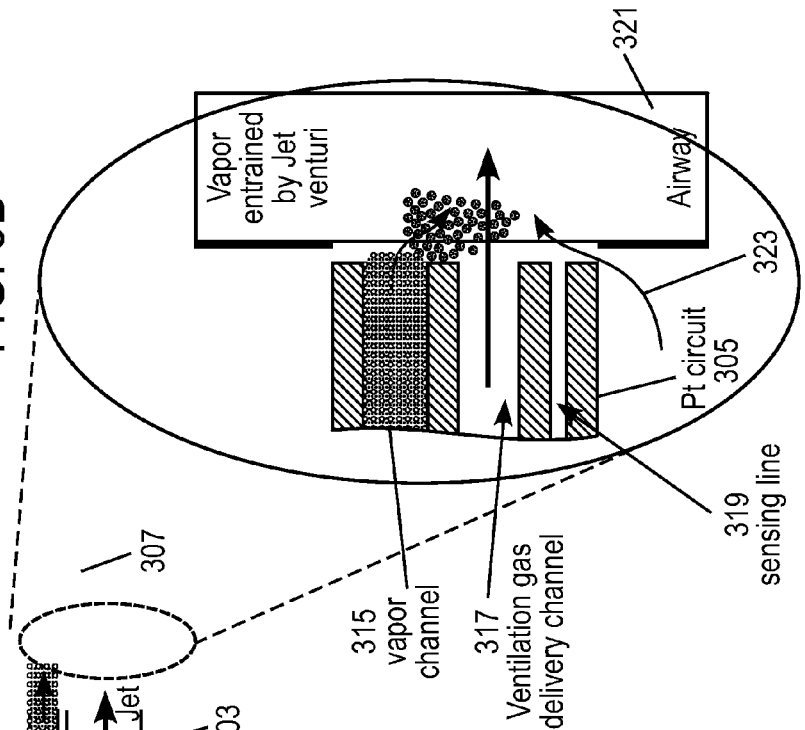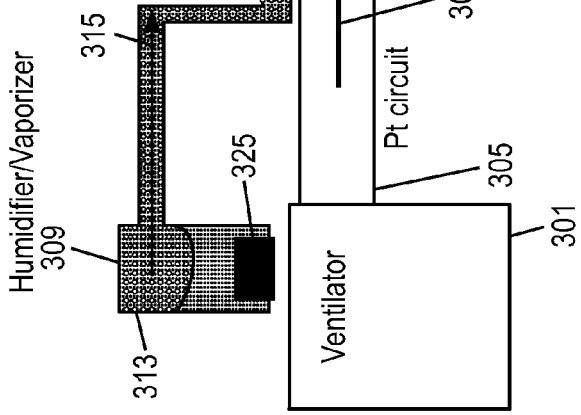

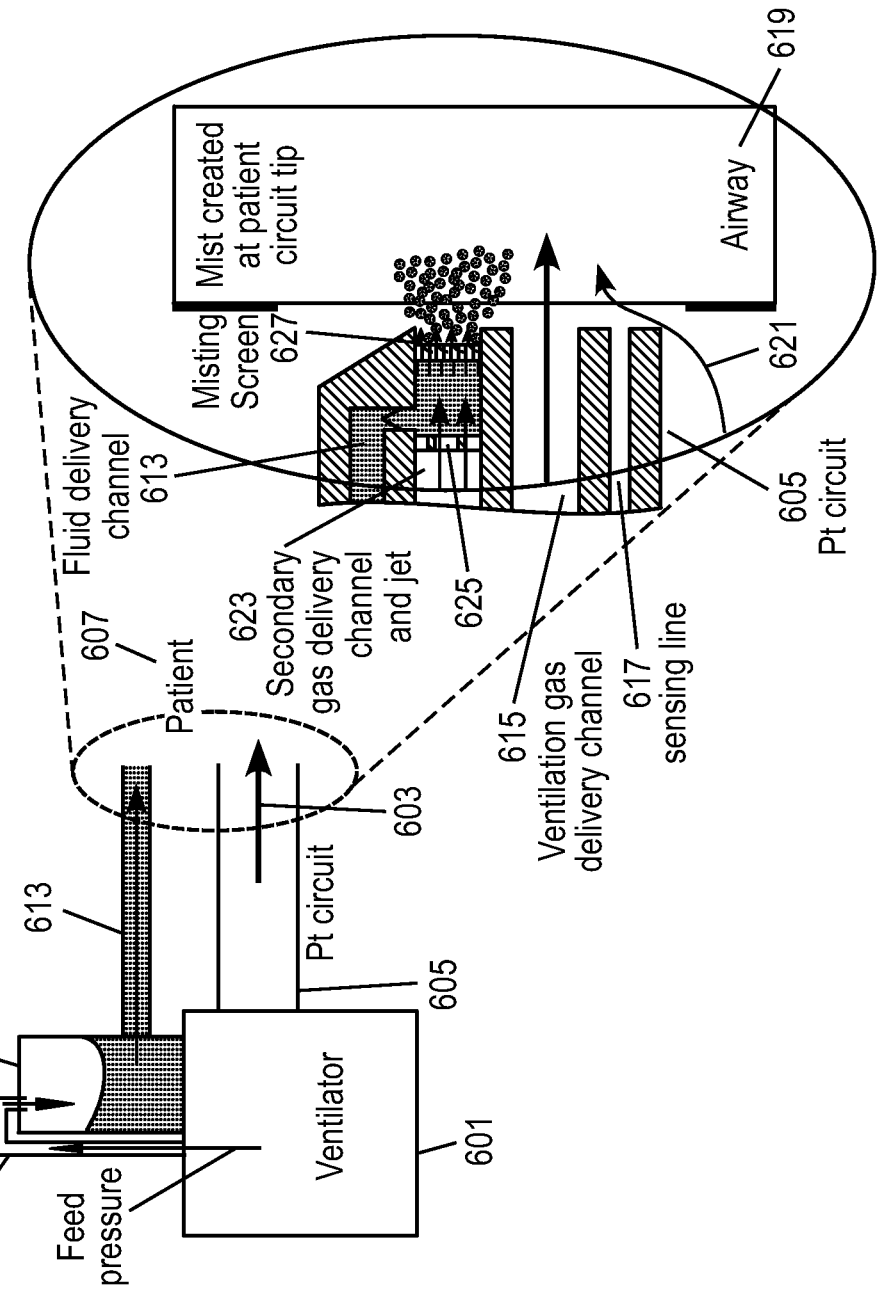

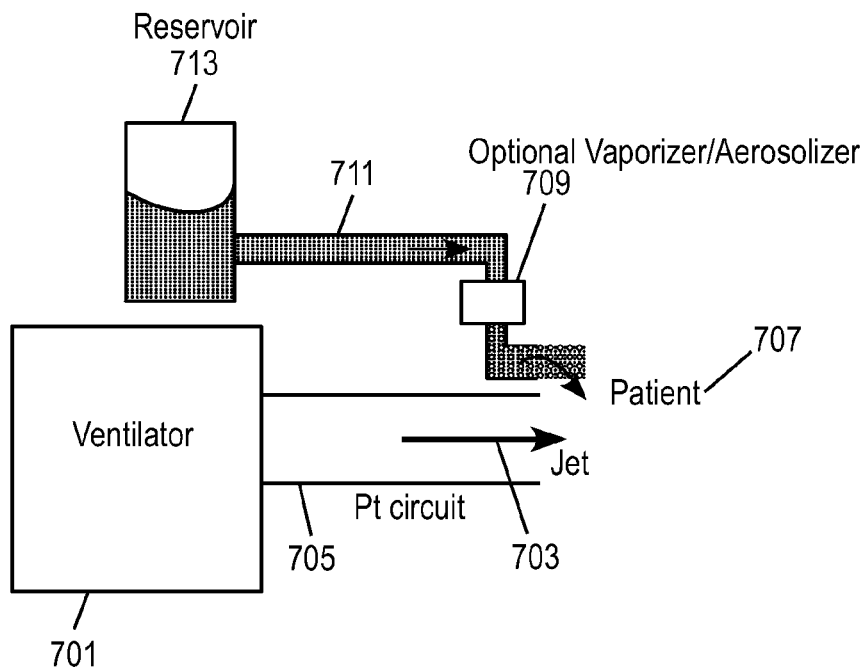
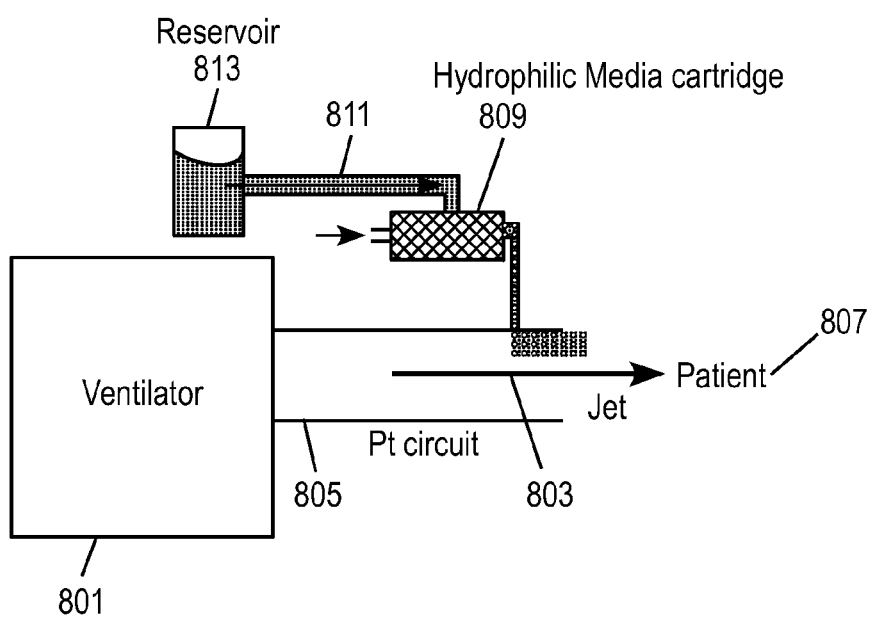

Gas Flow 1403
Fluid Channel 1401

Aerosol delivered to patient interface or directly to airway

Ventilation gas delivery channel sensing line

Pt circuit

Airway

FIG. 14B

Gas Flow 1405
Fluid Channel 1407

Aerosol delivered to patient interface or directly to airway

Ventilation gas delivery channel sensing line

Pt circuit

Airway

METHODS, SYSTEMS AND DEVICES FOR HUMIDIFYING A RESPIRATORY TRACT

CROSS-REFERENCE TO RELATED APPLICATIONS

This application claims priority to U.S. Provisional Patent Application No. 61/388,528, filed Sep. 30, 2010; the content of which is incorporated herein by reference in its entirety.

FIELD OF THE INVENTION

The present invention relates to the field of ventilation therapy for persons suffering from respiratory and breathing disorders, such as respiratory insufficiency and sleep apnea. More specifically, the present invention relates to methods and apparatus for providing humidification to a patient receiving artificial ventilation.

BACKGROUND OF INVENTION

There are a range of clinical syndromes that require some form of ventilation therapy. These syndromes may include hypoxemia, various forms of respiratory insufficiency, and airway disorders. There are also non-respiratory and non-airway diseases that require ventilation therapy, such as congestive heart failure and neuromuscular disease, respectively. Typically, patients receiving gas through these ventilation therapy systems require the addition of humidification to the gas being delivered to prevent the gas from drying the airways. Additionally, it is also known that with oxygen therapy, if oxygen is delivered for an extended time at flow rates greater than 6 lpm, the airways will dry, and artificial humidification is required.

In existing systems, humidification is added by passing the delivered gas through the vapor phase of a humidifier or bubbling the gas through water. For mechanical ventilators, the gas delivery tubing, or patient circuit, that fluidly transmits the breathing gas from the ventilator to the patient in existing systems is sized to provide for low pressure drop between the ventilator and the patient. This tubing is sized at 15 mm or 22 mm inside diameter. To prevent the vapor from condensing within the tubing, an adjunctive technique of heating the gas delivery tubing or thermally insulating it with protective sheathing is commonly applied.

A new generation of mechanical ventilators is emerging that utilizes smaller tubing to transport the breathing gas to patients. The gas delivery tubing of this new generation of ventilators is in the range of 2-14 mm inside diameter, compared to 15 mm or 22 mm inside diameter for currently available systems. Correspondingly, the pressures achieved within the new gas delivery tubing can be 0-80 psig higher than ambient pressure, whereas the pressure inside of tubing from currently available ventilators is typically within 1 psig of ambient pressure. Due to the smaller diameter and higher pressure of the gas delivery circuit of newer mechanical ventilator systems, there is a corresponding need for new humidification systems.

Additionally, some of the new generations of mechanical ventilators utilize an open airway technology, wherein the air passage between the ventilator and the patient is not sealed, as it is in traditional mechanical ventilator systems. The systems utilizing open airway technology provide for ambient air to be entrained near the patient interface via a venturi system in addition to the gas delivered from the ventilator, wherein the gas delivered to the patient is the combination of the gas delivered from the ventilator plus the entrained air. With the newer open systems, it may be challenging and inefficient to add humidification to the delivered gas using conventional methods. Therefore, a need exists for new humidification technologies compatible with the open airway technology.

Furthermore, the new generations of mechanical ventilators are designed to emphasize use during walking and mobility, whereas existing ventilation systems tend to limit mobility to applications such as when patients are confined to a wheelchair. Existing humidification systems typically use water tubs that are large and orientation sensitive, and are typically heated by systems that consume more power than is practical to power by a portable battery source. For these reasons, existing systems are typically only used to provide humidification when the patient is stationary. Therefore, an additional need exists for humidification technologies that are small, lightweight and portable.

Existing humidification systems typically do not have precise control of the amount of water introduced into the system, and they are not synchronized with the patient's breathing patterns. Typically, existing systems can provide humidification levels above 90% relative humidity, even though some studies have shown that patients typically cannot perceive a benefit for humidification levels above 50% relative humidity. Additionally, because existing systems either have continuous intentional leaks or exhalation flows, and because patients nominally exhale twice as long as they inspire, existing humidification systems can consume up to three times the water that is required if the systems only provided water during the patient's inspiratory cycle. Additionally, by providing more humidification than is required by the patient's needs, existing humidification systems often have problems with excessive "rainout" or condensation in the tubing, leading to the requirement of water traps in the tubing to catch excess water to prevent adverse effects due to patients and equipment aspirating water that collects in the system. Additionally, when used during sleep, some patients complain of the existing humidification systems soaking their pillows with water because of the excess humidity provided. For these and other reasons, an additional need exists for humidification systems that can precisely control the amount of humidification added and/or to synchronize the humidification with the patients' breathing patterns.

Because existing systems typically heat water to vaporize it, they can experience performance degradations that are caused by solids that are left behind by other water sources containing dissolved solids, such as tap water, and for this reason, they typically require the use of distilled water with their systems. However, users of humidification systems would prefer not to have to deal with the expense and inconvenience of acquiring distilled water for their systems. Therefore, an additional need exists for humidification systems that do not require distilled or other specialized water.

SUMMARY OF INVENTION

The present invention solves the limitations of prior systems with unique features that allow delivery of humidification to small diameter, higher pressure, and open airway gas delivery circuits.

Embodiments of the present invention include a nasal interface apparatus for receiving ventilation gas from gas delivery tubing and for humidifying ventilation gas, the apparatus may include one or more channels within the nasal interface to deliver gas from a gas delivery circuit to one or more structures, wherein the one or more structures may be in fluid communication with the one or more channels to direct ventilation gas to the patient's nose; and a hygroscopic material within the nasal interface in the flow path of the ventilation gas.

In certain embodiments, the one or more structures may be one or more nasal pillows, and wherein the hygroscopic material may be located within the one or more nasal pillows or within a cushion attached to the one or more nasal pillows. At least one pressure sensor device may be provided, wherein the at least one pressure sensor is located on a patient side of the hygroscopic material. The gas delivery circuit may have an inside diameter of approximately 2-14 mm. The system may be used with a portable ventilation system. Delivery of the humidified ventilation gas may be servo controlled, wherein the servo controls humidification levels based on the patient's need, and wherein the servo predictively controls humidification levels. The servo may consider gas flow delivered to the patient, ambient temperatures, ambient humidity, and combinations thereof. The humidified ventilation gas may be delivered in synchrony with the patient's breathing cycle. More humidified ventilation gas may be delivered during the patient's inspiratory phase than during the patient's expiratory phase. Heated tubing may be provided. Energy may be applied to the heating tubing in synchrony with the patient's need and the patient's breathing cycle.

Embodiments of the present invention may include a method for delivering humidified ventilation gas, the method including providing a nasal interface including: one or more channels within the nasal interface to deliver gas from a gas delivery circuit to one or more structures, wherein the one or more structures are in fluid communication with the one or more channels to direct ventilation gas to the patient's nose; and a hygroscopic material within the nasal interface in the flow path of the ventilation gas; and delivering humidified ventilation gas to the patient.

In certain embodiments, the one or more structures may be one or more nasal pillows, and wherein the hygroscopic material may be located within the one or more nasal pillows or within a cushion attached to the one or more nasal pillows. At least one pressure sensor may be provided, wherein the at least one pressure sensor may be located on a patient side of the hygroscopic material. The gas delivery circuit may have an inside diameter of approximately 2-14 mm. Delivery of the humidified ventilation gas may be controlled with a servo. The humidified ventilation gas may be delivered in synchrony with the patient's breathing cycle.

Embodiments of the present invention may include a system for humidifying ventilation gas, the system including a ventilator; a patient circuit in fluid communication with the ventilator at a proximal end and fluidly connected to a patient airway at a distal end, wherein the patient circuit has an inner diameter of approximately 2-14 mm; a fluid reservoir; a humidification device; and a channel between the humidification device and a distal end of the patient circuit.

In certain embodiments of the present invention, a patient interface may be provided, wherein the patient interface may be a nasal interface, an oral interface, or a transtracheal interface. The fluid may be water, a drug solution, or combinations thereof. A drug may be delivered alternatively with humidification. The ventilator may be portable. The channel may end proximal to an end of the patient circuit, such that a jet venturi created by the gas in the patient circuit entrains vapor from the channel. The fluid reservoir may be pressurized by gas from the ventilator. A misting screen may be provided at a distal end of the channel. A second channel may be provided for delivering gas to create a jet prior to the misting screen. A hydrophilic media cartridge may be provided within the channel. A capillary force vaporizer may be provided. A vibrating mesh nebulizer may be provided. An aerosolizing catheter may be provided. A gas flow channel surrounding the channel may be provided. The channel may surround a gas flow channel. A vortex heat separator may be provided for providing hot gas to a humidifier and cold gas to the ventilator. Delivery of the humidified ventilation gas may be servo controlled. The humidified ventilation gas may be delivered in synchrony with the patient's breathing cycle. An average flow rate of gas delivered by the ventilator may be greater than approximately 6 lpm. The delivery of humidified gas may be controlled to within 50 to 95% relative humidity to prevent rainout within the patient circuit.

Embodiments of the present invention may include a method of treating respiratory and breathing disorders, the method including: providing a ventilation system comprising: a ventilator; a patient circuit in fluid communication with the ventilator at a proximal end and fluidly connected to a patient airway at a distal end, wherein the patient circuit has an inner diameter of approximately 2-14 mm; a fluid reservoir; a humidification device; and a channel between the humidification device and a distal end of the patient circuit; and providing ventilation gas to a patient.

Certain embodiments may include controlling delivery of the humidified ventilation gas with a servo. The humidified ventilation gas may be delivered in synchrony with the patient's breathing cycle. A drug solution may be delivered alternatively with the humidified ventilation gas. An average flow rate of gas delivered by the ventilator may be greater than approximately 6 lpm.

Embodiments of the present invention may include an apparatus for delivering humidified ventilation gas, the apparatus including: one or more tubes with an inner diameter of approximately 2-14 mm; and one or more heaters along the length of the one or more tubes, wherein the one or more tubes are adapted to deliver humidified ventilation gas to a patient.

Certain embodiments may include the one or more heaters controlled by a controller to deliver heat in synchrony with the patient's need and the patient's breathing cycle. The one or more heaters may be controlled by a controller to deliver heat in based on environmental conditions.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTIONS OF THE FIGURES

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 2A shows a prior art pass-over or pass-through bubble system.

FIG. 2B shows an enlarged view of the prior art pass-over or pass-through bubble system of FIG. 2A.

FIG. 2C shows a modified version of the humidity system of FIG. 2A.

FIG. 3A shows a vapor entrainment system, according to an exemplary embodiment.

FIG. 3B shows an enlarged view of the vapor entrainment system of FIG. 3A.

FIG. 6A shows a moisture feed misting system, according to an exemplary embodiment.

FIG. 6B shows an enlarged view of the moisture feed misting system of FIG. 6A.

FIG. 7 shows a moisture entrainment system, according to an exemplary embodiment.

FIG. 8 shows a cartridge entrainment system, according to an exemplary embodiment.

FIG. 10 shows an embodiment with a capillary force vaporizer, according to an exemplary embodiment.

FIG. 11A shows an embodiment with a nebulizer, according to an exemplary embodiment.

FIG. 12 shows an embodiment with an aerosolizer, according to an exemplary embodiment.

FIG. 14A shows an embodiment for delivering humidified gas using additional gas flow channels, according to exemplary embodiment.

FIG. 14B shows a detail of an alternative embodiment of FIG. 14A, according to an exemplary embodiment.

DETAILED DESCRIPTION OF THE EMBODIMENTS

Figure 1:
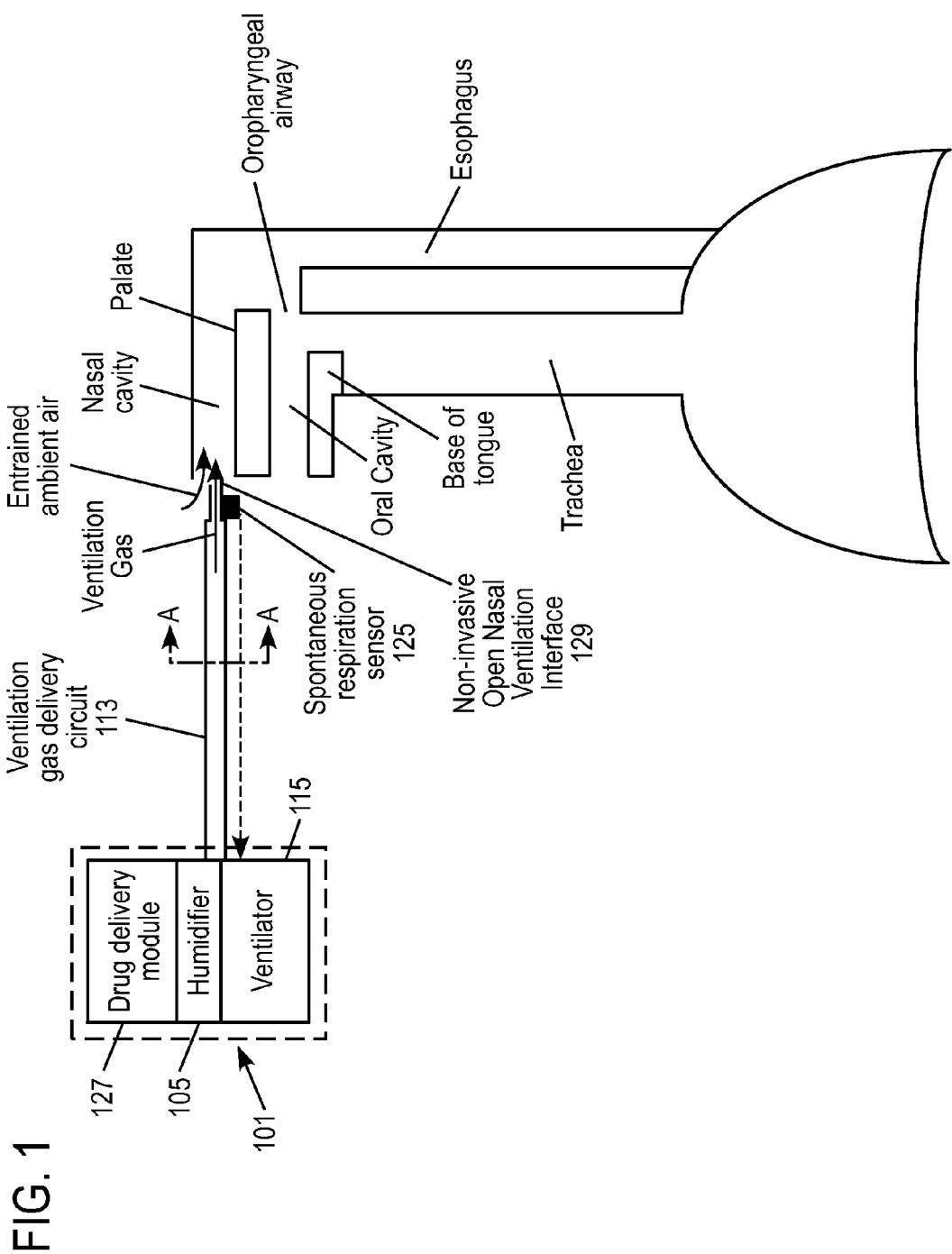
FIG. 1 is a system schematic of the invention, according to an exemplary embodiment.
Figure 4:
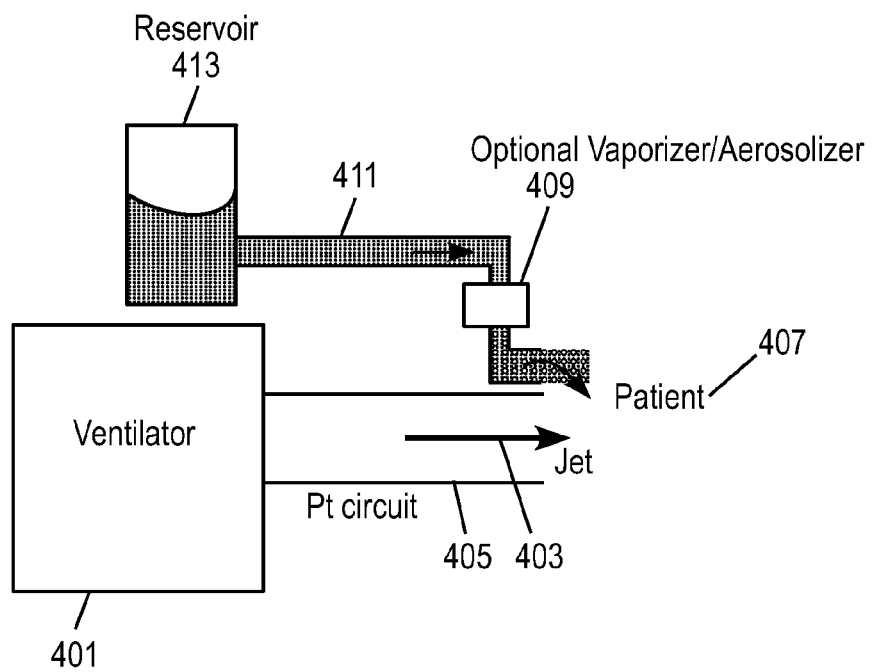
FIG. 4 shows an aerosolization system, according to an exemplary embodiment.

A humidification system is described for use in conjunction with a ventilation therapy system. The humidification system may be suited for integration into a small-bore, high-pressure ventilation gas delivery system. It can be appreciated that while the invention applies to the above application, this invention may have inherent advantages over conventional artificial humidification systems, and, as such, can also be applied to conventional ventilation systems, and to oxygen therapy systems, as well as drug delivery systems.

The humidification system can be used in conjunction with a patient interface, which may include a full face, nasal, oral, or transtracheal patient interface.

The humidity and/or aerosol can be added to the patient interface, such as the nasal mask or transtracheal tube, or can be applied directly to the airway, or can be applied to the gas delivery circuit conducting the ventilation gas to the patient. The humidity or aerosol can be delivered in parallel with the ventilation gas, or can be combined with the ventilation gas. Ideally, the humidity particles are less than 15 microns if being generated remotely and delivered, or less than 20 micron if generated near the entry to the patient airway, to not conduct bacteria to the airway. An average flow rate of gas delivered by the ventilator may be greater than approximately 6 lpm.

Humidification can be added to the gas delivery circuit by active heated humidification or aerosolizing moisture particles into the gas delivery system, typically into or from the patient interface mask or connection, or a heat moisture exchange (HME), or combinations thereof.

To prevent rainout from occurring in the interface mask or connection, the mask or connection may have a drainage line to scavenge any moisture that is collecting.

Embodiments of the present invention may improve humidification to decrease water consumption and improve mobility of patients. General concepts applicable to all active humidification systems may include delivery of moisture timed with patients' breathing patterns. Use of heated tubing may be provided. Heated tubing may be fixed, controlled by environmental conditions, timed by breathing patterns, and/or served to breathing patterns.

Embodiments of the present invention may also address humidification within small tubes, generally less than 15 mm inner diameter. Small inner diameter tubes typically are characterized by high pressure delivered by a blower/ventilator, and a high pressure drop along the tube.

Within small tube systems, traditional humidification systems are described herein. Traditional may refer to systems that do not rely on entrainment for developing fluid flow through the system. According to embodiments of the present invention, pressure drop along a tube makes the relative humidity percentage decrease. This effect may counterbalance the increase of relative humidity percentage due to the cooling of the gas along the length of the tube. The result may be that rainout is prevented and gas with relative humidity percentage between about 50 and about 99 is delivered to the patient. In preferred embodiments, the delivery of humidified gas is controlled to within 50 to 95% relative humidity to prevent rainout within the patient circuit.

Within small tubes, entrainment systems are described herein. Generally, the flow of breathable gas to the patient (Qp) is made of (1) flow from the ventilator (Qjet) that creates the entrainment effect, and (2) entrained flow (Qent). Humidification of the entrained gas (Qent) may be humidified directly. Alternatively or additionally, the flow from the ventilator (Qjet), which may be air, oxygen, etc., may be humidified. Benefits of humidifying the flow of breathable gas (Qjet) may include increasing the density of the gas delivered to the patient, which may increase the entrainment effect. A humidification device or system may be positioned anywhere along the flow path of the breathable gas (Qjet), from before a ventilator up to an entrainment nozzle itself The humidification liquid may or may not be heated. If heated by the humidification system, the humidification system may use a capillary forced vaporizer. If not heated by the humidification system, the flow of breathable gas (Qjet) may or may not be heated by a separate heater. In these configurations, the humidification system may use a hydrophilic media cartridge with additional water feeding line, an ultrasonic nebulizer, an airbrush-style aerosol generator (where a high speed jet of gas entrains liquid and nebulizes the liquid), vibrating mesh nebulizer, etc.

In embodiments of the present invention, humidification may be provided within a patient interface using direct moisture delivery technology, moisture reuse technology, and/or a combination thereof.

Direct moisture delivery technologies may be provided in the patient interface. The humidification liquid may or may not be heated. If heated by the humidification system, the humidification system may use a capillary forced vaporizer. If not heated by the humidification system, the flow of breathable gas (Qjet) may or may not be heated by a separate heater. In these configurations, the humidification system may use a hydrophilic media cartridge with additional water feeding line, an ultrasonic nebulizer, an airbrush-style aerosol generator, vibrating mesh nebulizer, etc.

Reuse of moisture may be provided in the patient interface. No external moisture may be required for this type of system. A moisture reuse system may be positioned within a manifold, within a nasal pillow, and combinations thereof. In particular, a heat and moisture exchanger may be used within one or more nasal pillows. For accurate sensor readings, a pressure sensor device may be located proximal to the patient, between the patient and a heat and moisture exchanger. Additional benefits of moisture reuse systems may include diffused venting of air streams and/or muffling that may result in reduced noise.

Combinations of humidification technology may also be used to improve water efficiency. For example, a heat and moisture exchanger may be combined with a hydrophilic cartridge fed with water, which may be pre-heated or not pre-heated.

FIG. 1 is a block diagram describing a ventilation system 101 using an embodiment of the invention. The ventilation system 101 may typically provide air, oxygen or some combination thereof to a patient, but could additionally provide alternate therapeutic gases. The ventilation system 101 can be self-contained with a battery and gas supply to enable it to be borne by the patient, so that the patient can ambulate and participate in activities of daily living. A ventilator 115 may provide ventilation gas. Other optional features of the ventilation system 101 may include a transmitter/receiver, pedometer, actigraphy sensor, a pulse oximeter, a $CO_2$ monitor, a blender, a pressurized air supply or generator, a liquid oxygen (LOX) system, a respiration sensor, etc.

A humidifier 105 can be integral or external to the ventilation system 101. However, unlike prior systems, humidified gas can be delivered through the gas delivery channel of the gas delivery circuit, through another lumen in the gas delivery circuit, or through a separate cannula or tubing. For extended use, when the patient is likely to be stationary, the humidification system can be a stationary system and capable of delivering a relative high amount of humidity, and for periods of mobility, the patient can either not receive humidification, or use a portable humidification system that is capable of delivering relatively a small amount of humidity, due to size and energy consumption constraints. Also unlike prior systems, some of the humidification techniques disclosed in this invention can be synchronized with the patient's breathing and the humidity introduced into the system can be precisely controlled, thereby reducing the quantity of water required by the system, reducing the amount of condensation in the system, and reducing the amount of power required to drive the system.

The ventilation system 101 may be portable, for example, less than about 10 pounds, and may have small bore tubing, for example, with an inner diameter less than 15 mm. Traditional humidification systems are not portable and utilize large bore tubing (typically 15 mm or 22 mm ID). Portability and small-bore tubing create unique issues when delivering humidification.

A drug delivery module 127 can optionally be incorporated internally or externally to the ventilator system 101. Due to challenges with current aerosolized drug delivery inhalers, the present invention can be used to propel and deposit medication particles deep in the respiratory system, without a carrier propellant. Because a patient's using the therapy often also requires prescription medication, this may be a convenient and efficient way to administer the medication. The drug delivery module 127 may deliver drugs together with humidification, alternatively with humidification, or combinations thereof. A controller may determine and/or tailor when drugs are delivered by the drug delivery module 127.

Embodiments of the present invention may be used in systems that create an entrainment effect. FIGS. 2A-2C illustrate prior art pass-over or pass-through systems that entrain humidified gas and/or ambient air. FIGS. 3-10 illustrate how embodiments of the present invention are integrated into entrainment systems.

FIGS. 2A-2C show prior art pass-over or pass-through bubble systems. In FIG. 2A, a ventilator 201 delivers gas 203 through a patient circuit 205 to a patient 207. A pass-over 209 and/or a pass-through 211 may provide gas to a humidifier/vaporizer/aerosolizer 213. The humidifier/vaporizer/aerosolizer 213 may have water, an aqueous solution, etc. 215 and a vapor phase 217. For a pass-over 209, the gas may pass through the vapor phase 217 only. For a pass-through 211, the gas may pass through the liquid phase 215 and/or the vapor phase 217. The gas may collect vapor or moisture in the humidifier/vaporizer/aerosolizer 213. Humidity may be created using a heated humidifier or an aerosolizer. Some aerosolizers may self-generate a flow source. Vapor may reach the patient without a flow source due to expansion. After exiting the humidifier/vaporizer/aerosolizer 213, the humidified gas may pass through a vapor channel 219.

As shown in FIG. 2B, the vapor channel 219 may be located proximal to the ventilation gas delivery channel 221. One or more sensing lines 223 may be present proximal to the patient circuit 205 to sense various parameters, such as pressure, temperature, humidity, flow, respiration, etc. In the particular embodiment of FIG. 2B, the distal end of the patient circuit 205 may terminate outside the patient airway 225. The delivery of gas 203 may entrain ambient air 227 into the patient airway 225. Alternatively, the patient circuit 205 may terminate at or inside the patient airway 225.

FIG. 2C shows a pass-over 209 where the humidifier/vaporizer/aerosolizer 213 is separate from the ventilator 201. The humidifier/vaporizer/aerosolizer 213 and the ventilator 201 may be separate devices and/or integrated.

FIGS. 3A-3B illustrate a vapor entrainment system. In FIG. 3A, a ventilator 301 delivers gas 303 via a jet Venturi through a patient circuit 305 to a patient 307. A humidifier/vaporizer/aerosolizer 309 may have water, an aqueous solution, etc. 311 and a vapor phase 313. Humidity can be created using a heated humidifier or an aerosolizer 325. The heating or aerosolizing element can be in the reservoir or in the tubing to the patient. After exiting the humidifier/vaporizer/aerosolizer 309, humidified gas may pass through a vapor channel 315.

FIG. 3B is a detail of the patient end of the device. The vapor channel 315 may be located proximal to a ventilation gas delivery channel 317. One or more sensing lines 319 may be present proximal to the patient circuit 305 to sense various parameters, such as pressure, temperature, humidity, flow, respiration, etc. In the particular embodiment of FIG. 3B, the distal end of the patient circuit 305 may terminate outside a patient airway 321. The delivery of gas 303 may entrain ambient air 323 into the patient airway 321. Alternatively, the patient circuit 305 may terminate at or inside the patient airway 321. Humid gas may be draw into the patient airway 321 by the ventilator jet Venturi.

FIG. 4 shows an aerosolization system. A ventilator 401 may deliver gas 403 through a patient circuit 405 to a patient 407. Liquid may be fed to an aerosolizer/vaporizer 409 from a reservoir 413 through a conduit 411. From the aerosolizer/vaporizer 409, the liquid may create a vapor and a self-generated flow source that propels the vapor to the patient 407.

Figure 5:
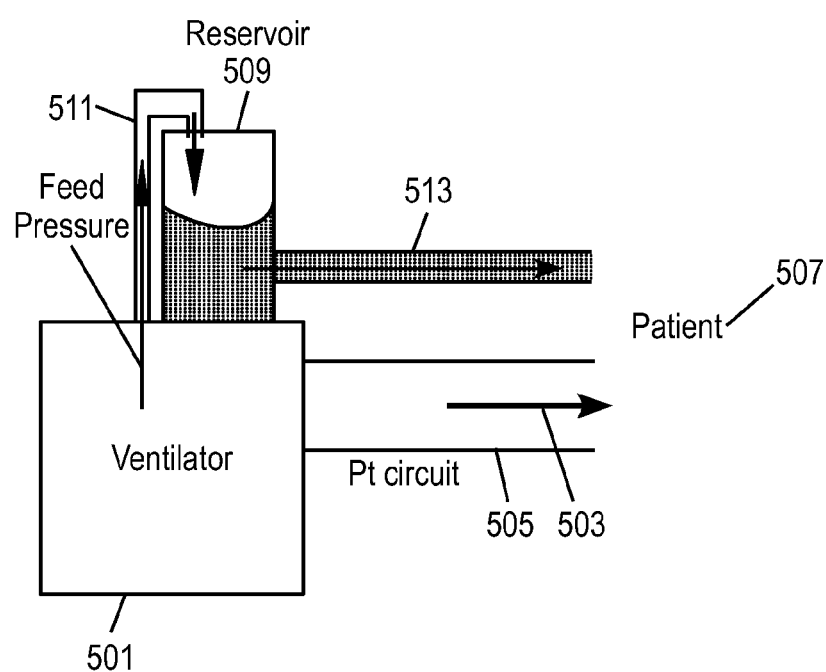
FIG. 5 shows a moisture feed system, according to an exemplary embodiment.

FIG. 5 shows a moisture feed system. A ventilator 501 may deliver gas 503 through a patient circuit 505 to a patient 507. The ventilator 501 may pressurize a reservoir 509 via a feed pressure conduit 511. Liquid droplets may be drawn from the reservoir 509 via a vapor channel 513 into the patient airway by a jet Venturi created by gas 503 exiting the patient circuit 505. The liquid may be aerosolized before it reaches the patient. The liquid may be heated or aerosolized with an element in the patient circuit 505.

FIGS. 6A-6B show a moisture feed misting system. As shown in FIG. 6A, a ventilator 601 may deliver gas 603 through a patient circuit 605 to a patient 607. The ventilator 601 may pressurize a reservoir 609 via a feed pressure conduit 611. Liquid droplets may be drawn from the reservoir 609 via a fluid delivery channel 613 into the patient airway by a jet Venturi created by gas 603 exiting the patient circuit 605. The liquid may be aerosolized before it reaches the patient. The liquid may be heated or aerosolized with an element in the patient circuit 605. FIG. 6B is a detail of the patient end of the device. The fluid delivery channel 613 may be located proximal to a ventilation gas delivery channel 615. A secondary gas delivery channel 623 and/or jet 625 may create a mist at a misting screen 627. One or more sensing lines 617 may be present proximal to the patient circuit 605 to sense various parameters, such as pressure, temperature, humidity, flow, respiration, etc. In the particular embodiment of FIG. 6B, the distal end of the patient circuit 605 may terminate outside a patient airway 619. The delivery of gas 603 may entrain ambient air 621 into the patient airway 621. Alternatively, the patient circuit 605 may terminate at or inside the patient airway 621. Humid gas may be draw into the patient airway 621 by the ventilator jet Venturi.

FIG. 7 shows a moisture entrainment system. A ventilator 701 may deliver gas 703 through a patient circuit 705 to a patient 707. Liquid may be fed to an aerosolizer/vaporizer 709 from a reservoir 713 through a conduit 711. From the aerosolizer/vaporizer 709, the liquid may be sucked to the patient 707 by a jet Venturi created by the ventilator 701. The liquid may be aerosolized before it reaches the patient 707, for example, using a Capillary Force Vaporizer (CFV), which does not require a gas flow source.

FIG. 8 shows a cartridge entrainment system. A ventilator 801 may deliver gas 803 through a patient circuit 805 to a patient 807. Liquid may be drawn or pressure fed to a hydrophilic media cartridge 809 from a reservoir 813 through a conduit 811. From the hydrophilic media cartridge 809, the liquid may be drawn out into the patient circuit 805 by a jet Venturi created by the ventilator 801.

Figure 9:
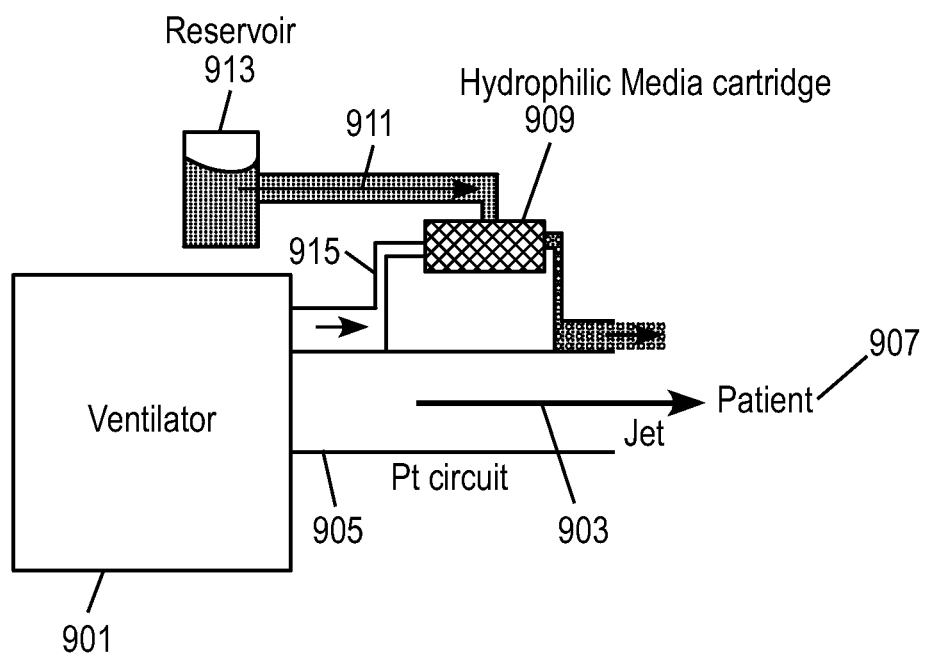
FIG. 9 shows a cartridge pass-through system, according to an exemplary embodiment.

FIG. 9 shows a cartridge pass-through system. A ventilator 901 may deliver gas 903 through a patient circuit 905 to a patient 907. Liquid may be drawn or pressure fed to a hydrophilic media cartridge 909 from a reservoir 913 through a conduit 911. A flow source, preferably from the ventilator 901, may be fed through a conduit 915 through the hydrophilic media cartridge 909. From the hydrophilic media cartridge 909, the liquid may be delivered to the patient 907 via a delivery conduit 917 separate from the patient circuit 905.

Figure 13A:
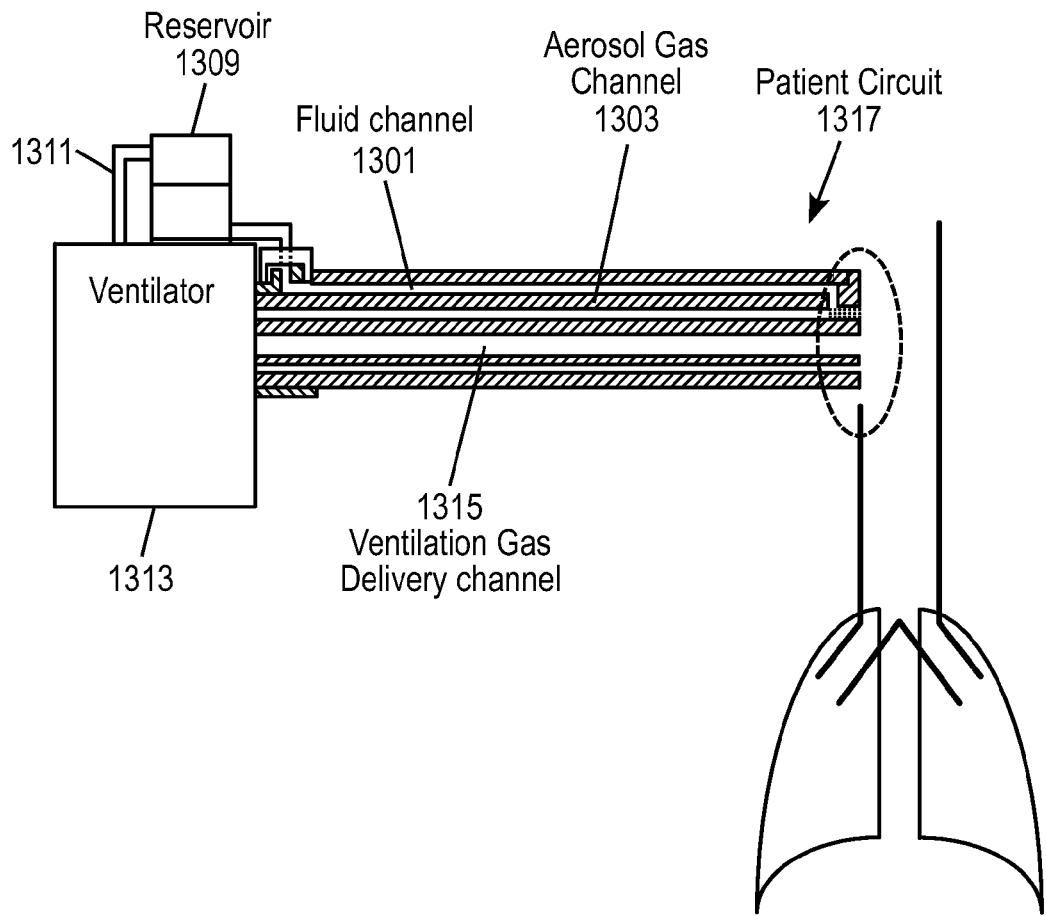
FIG. 13A shows an embodiment with aerosol gas channels, according to exemplary embodiment.
Figure 13B:
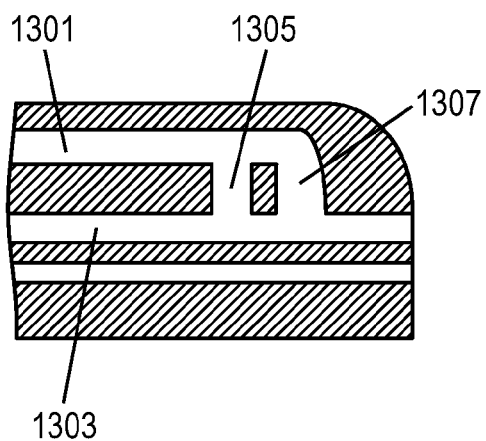
FIG. 13B shows a detail of an alternate gas delivery circuit distal end, according to an exemplary embodiment.

FIGS. 13A-13B show embodiments with aerosol gas channels. FIG. 13A shows a fluid channel 1301 entering an aerosol gas channel 1303 prior to exiting the device. The meeting of the gas with the fluid may create humidity. FIG. 13B shows an alternative embodiment with two conduits 1305, 1307 transferring fluid from the fluid channel 1301 to the aerosol gas channel 1303. Fluid may be drawn or pressure fed from a reservoir 1309 that may be pressurized via a conduit 1311 in fluid communication with a ventilator 1313. A ventilation gas delivery circuit 1315 may deliver gas through a patient circuit 1317.

Embodiments of the present invention may also be integrated into or used with non-entrainment-based systems.

Figures 10, 11A, 12:
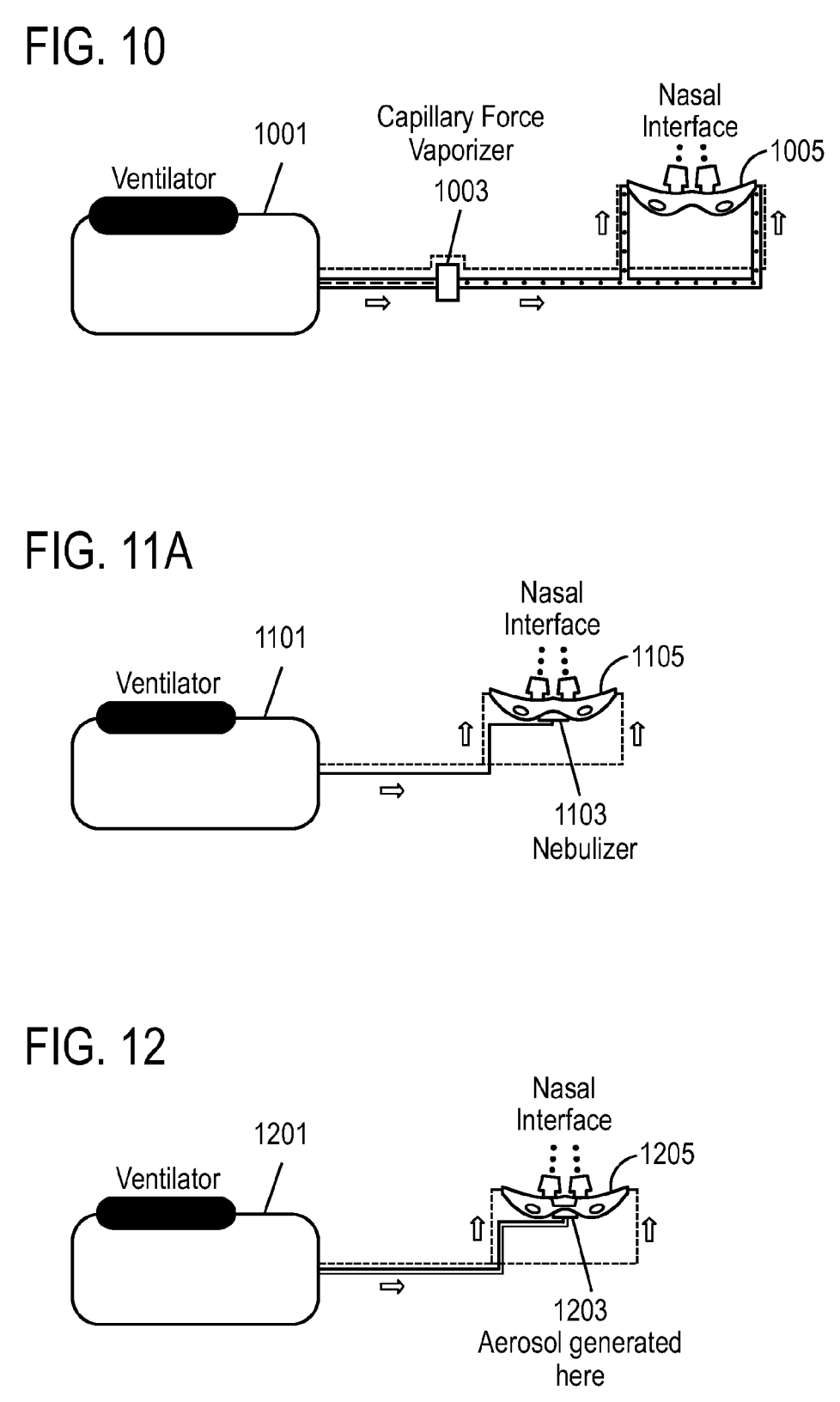

FIG. 10 shows an embodiment of a ventilator 1001 with a capillary force vaporizer 1003 feeding vaporized gas to a patient interface 1005. A capillary force vaporizer 1003 is a subsystem that wicks liquid from a liquid reservoir into a miniaturized heating element where the liquid is converted to a heated vapor. The capillary force vaporizer may be located proximal to the ventilator, in the patient interface, or in the patient circuit. In the preferred embodiment, the capillary force vaporizer is located proximal to the ventilator and the vapor is delivered to the patient interface via the patient circuit along with the flow from the ventilator. To prevent the vapor from condensing in the tubing, the tubing can be heated or the patient circuit can have features to insulate the walls of the patient circuit from ambient temperature.

Figure 11B:
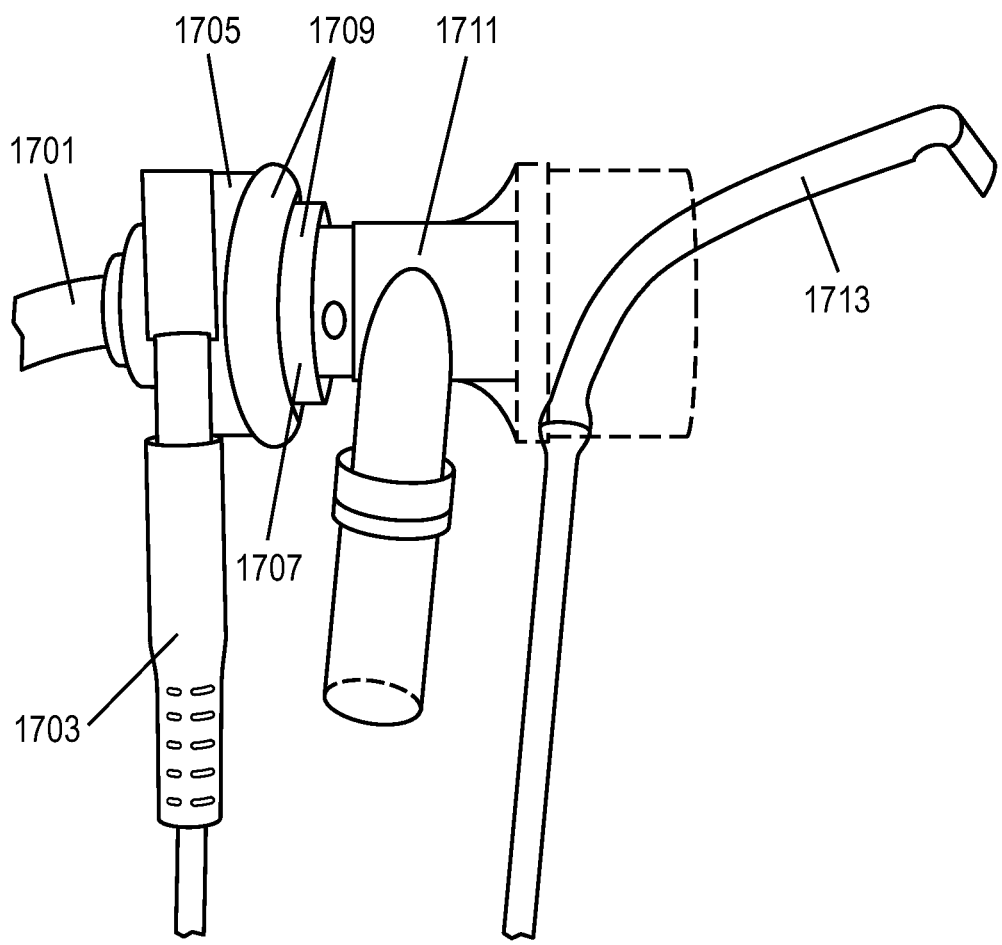
FIG. 11B shows an exemplary humidification system, which may be used with the nebulizer system of FIG. 11A.
Figure 11C:
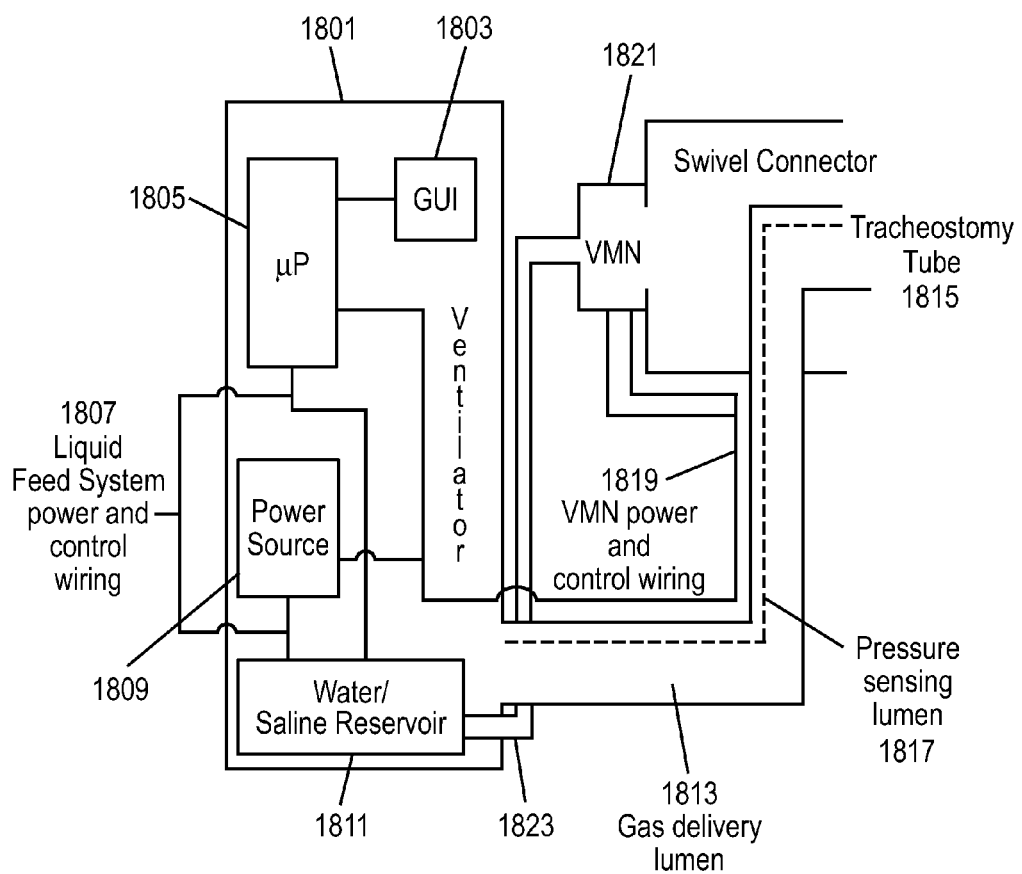
FIG. 11C is a schematic of a humidification system as shown in FIG. 11B.

FIG. 11A shows an embodiment of a ventilator 1101 with a nebulizer 1103, such as a vibrating mesh nebulizer or ultrasonic nebulizer, feeding nebulized humidification to a patient interface 1105. The nebulizer 1103 may be located proximal to the ventilator, in the patient interface, or in the patient circuit. In the preferred embodiments, the nebulizer is located in the ventilator and the vapor is delivered to the patient interface via the patient circuit along with the flow from the ventilator. If the nebulizer is located proximal to the ventilator, the tubing can be heated to assist in the conversion of the nebulized liquid to vapor and to provide a comfortable temperature gas to the patient. FIGS. 11B and 11C show an embodiment of a vibrating mesh nebulizer located at the patient interface for an open airway ventilation system.

FIG. 11B shows an exemplary humidification system. Features of a connector may include a syringe-powered liquid feed system 1701, power and control wiring 1703, a vibrating mesh adapter 1705, rapid prototyped adapter 1707, openings 1709 to increase aerosol flow, a modified swivel connector 1711, and/or a ventilator patient circuit 1713.

FIG. 11C is a schematic of a humidification system as shown in FIG. 11B. A ventilator 1801 may include a graphical user interface 1803, a processor 1805, a liquid feed system power and wiring device 1807, a power source 1809, and/or a liquid reservoir 1811. A gas delivery lumen 1813 may lead to a tracheostomy tube 1815. A pressure sensing lumen 1817 may also run from the ventilator 1801 to a tracheostomy tube 1815. Vibrating mesh nebulizer power and control wiring 1819 may lead from the ventilator 1801 to a vibrating mesh nebulizer 1821. The vibrating mesh nebulizer 1821 may be in fluid communication 1823 with the liquid reservoir 1811. A swivel or other type of connector 1825 may couple the vibrating mesh nebulizer 1821 with the tracheostomy tube 1815.

FIG. 12 shows a ventilator 1201 with an aerosolizing catheter 1203 feeding aerosolized gas to a patient interface 1205. An aerosolizing catheter 1203 is a subsystem that transports liquid from a liquid reservoir to a miniaturized aerosolizing tip where the liquid is converted to an aerosol. A driving pressure is used to feed liquid through the aerosolizing catheter and create the aerosol. In a preferred embodiment, pressure from the ventilator is used to create the driving pressure. The aerosolizing catheter can either be inserted into the patient circuit, or incorporated into the patient circuit such that the patient circuit has a lumen dedicated to transporting liquid from the liquid source to the aerosolizing tip. The aerosolizing tip may be located proximal to the ventilator, in the patient interface, or in the patient circuit. In the preferred embodiment, the aerosolizing tip is located proximal to the patient interface or within the patient interface, such that the aerosol is delivered to the patient with minimal interaction between the aerosol and the walls of the patient interface. To optimize patient comfort, the portion of the aerosolizing catheter that transports liquid from the liquid reservoir to the aerosolizing tip may be heated.

FIGS. 14A-14B show embodiments for delivering humidified gas using additional gas flow channels. In FIG. 14A, a fluid channel 1401 may be surrounded by a gas flow channel 1403, which may terminate at substantially the same position as the fluid channel 1401. At the termination point of the channels 1401, 1403, the fluid may be aerosolized and delivered to a patient interface or directly to an airway. In FIG. 14B, a gas flow channel 1405 may be surrounded by a fluid channel 1407, which may terminate at substantially the same position as the gas flow channel 1405. At the termination point of the channels 1405, 1407, the fluid may be aerosolized and delivered to a patient interface or directly to an airway. In an additional embodiment, either the system constituted by 1403 and 1401 or 1405 and 1407 can concentric to the ventilation gas delivery channel at the entrainment port location or, more generally, can be the jet portion of the venturi pump. In this embodiment, the gas flow 1403 or 1405 will aerosolize the fluid in the channels respectively 1401 and 1407. The resulting aerosolized mixture of fluid and gas will be the jet that will entrain the air into the ventilation gas delivery channel. The increased density of the gas/aerosol mixture will provide an increase of entrainment performance, effectively entraining more air with the same gas flow Humidification sources, such as the capillary force vaporizer, vibrating mesh nebulizer and aerosolizing catheter, can be controlled to provide humidification levels that are dependent upon patient need. For instance, one or more humidification sensors can be located between the humidification source and the patient, and the amount of humidification added by these subsystems can be servo controlled to provide a target humidification level that meets the patient's needs but prevents rainout, for example, 75% relative humidity. Alternately, the humidification subsystem can be characterized such that the control system can predictively set the output of the humidification source based on known characterization of the humidification subsystem and other variables such as the gas flow delivered to the patient, ambient temperature, ambient humidity, and combinations thereof. The controller for the humidification system can be a standalone subsystem, or in a preferred embodiment, can be integrated with the ventilator.

Preferably, the humidification sources can be controlled in synchrony with the patient's breathing cycle, such that more humidity is added during the patient's inspiratory phase and less or no humidity is added during the patient's expiratory phase. Those skilled in the art would recognize that the large bore tubing used in practice today contains a large internal volume (approximately 750 ml for 22 mm tubing), making it challenging or impossible to synchronize humidity levels with the patient's breathing pattern at the patient connection port while providing humidification at the ventilator end of the tubing because of the very significant phase delay introduced by the tubing. By comparison, the internal volume of small bore tubing embodied in this invention (approximately 50 ml for 6 mm tubing) introduces only minimal inaccuracies due to phase delay.

The main cause of "rainout", or condensation of water within the delivery tube, is the increase of the relative humidity above saturation due to the cooling of the humidified breathable gas flowing into the delivery tube. The use of small bore tubing requires high pressure levels (40 psig or higher) to be generated by the mechanical ventilator to obtain appropriate treatment pressure values at the patient interface. The high pressure drop along small bore tubes may be employed to counteract the increase of relative humidity that leads to water condensation as mentioned above. As the pressure of the breathable gas decreases from the patient distal to the proximal portions of the delivery tube, the relative humidity decreases correspondingly. This effect is used to keep a high and constant relative humidity, making sure that no condensed water forms in the delivery tube. The magnitude of this effect is dependent on the actual flow delivered to the patient since the higher the required flow, the higher the pressure drop along the delivery tube and the higher the pressure generated by the ventilator must be. The heat loss along the tube is also dependent upon the flow rate of the gas; in particular it may be lower at lower flow rates. At low flow rate values, the increase of relative humidity due to temperature drop of the breathable gas may be lower, as well as the decrease of relative humidity due to the pressure drop along the delivery tube. The opposite may happen at higher flow rates. This mechanism of compensation of the two mentioned effects may be naturally synchronized with the breathing cycle of the patient. The effect may only be used when small bore tubes are utilized since bigger bore tubes (15 mm ID or more) may not require pressure levels where this phenomenon is of appreciable magnitude.

Additionally, if heated tubing is utilized, the energy applied to the heater can be controlled in synchrony with the patient's needs and breathing cycle, allowing for a highly optimized system. Heated tubes preferably are small-bore tubes with an inner diameter of approximately 2-14 mm. One of skill in the art would understand that heated tubes can employ electrical elements to provide heat. The electric power provided to the heater can be synchronized with the patient breathing cycle and/or humidity needs during the breathing cycle. The use of small bore tubes may provide a small thermal inertia to the system, effectively allowing a fast response and precise temperature/humidity control of the gas delivery system.

Figure 15:
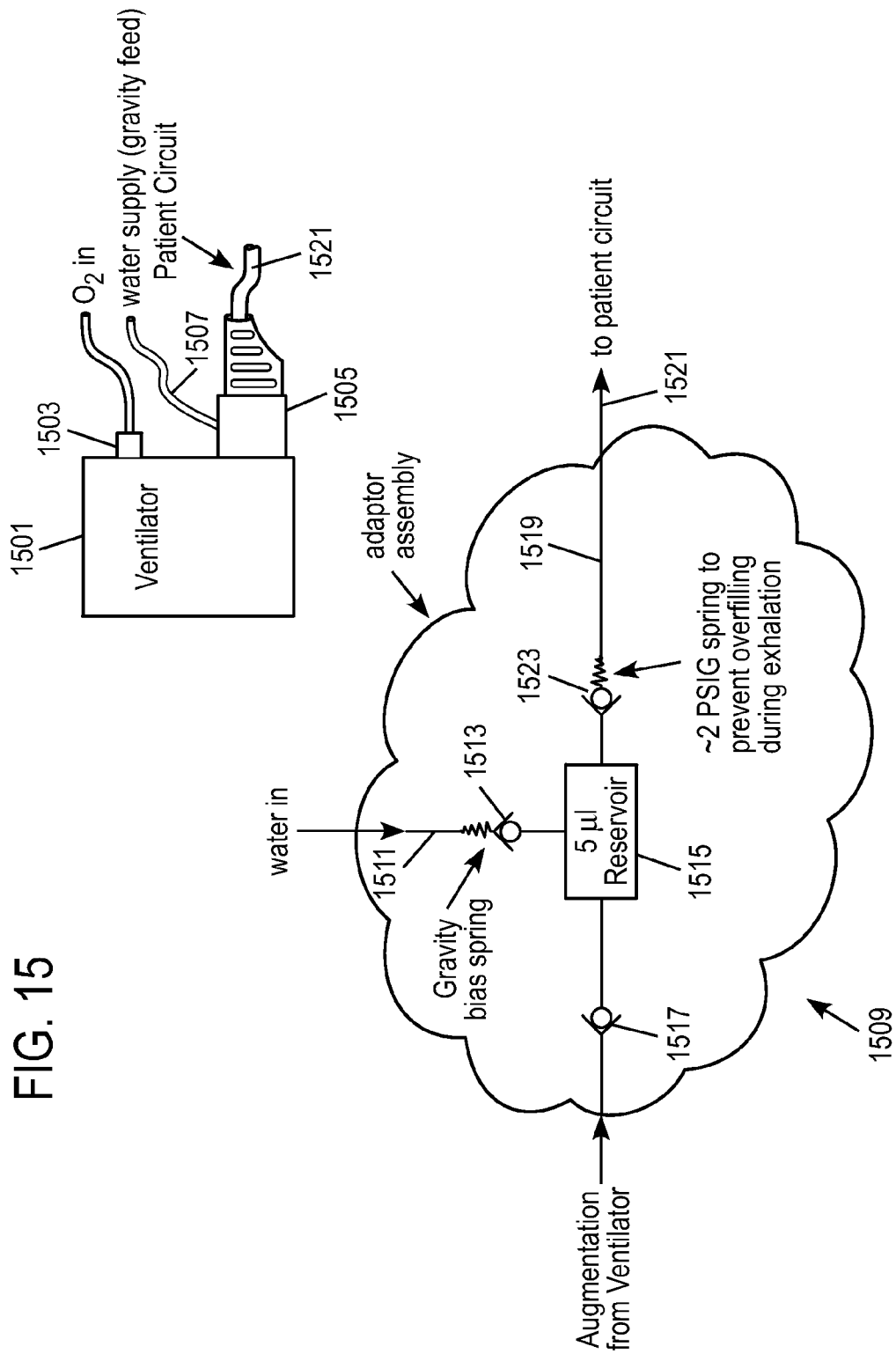
FIG. 15 shows a humidification system for a ventilator, according to an exemplary embodiment.

FIG. 15 shows a humidification system for a ventilator. A ventilator 1501 may include an oxygen input 1503 a patient circuit output 1505. A water supply 1507 may be included, which may be gravity fed. The patient circuit output 1505 may include a humidity adapter assembly 1509. A water inlet 1511 may lead to a bias spring 1513 or similar device, which may then lead to a reservoir 1515. The reservoir may be approximately 5 ml or any other appropriate size. Augmentation from the ventilator 1501 may be fed 1517 into the reservoir 1515. An output 1519 may be provided to a patient circuit 1521. An approximately 2 psig spring 1523 may prevent overfilling during exhalation.

Figure 16:
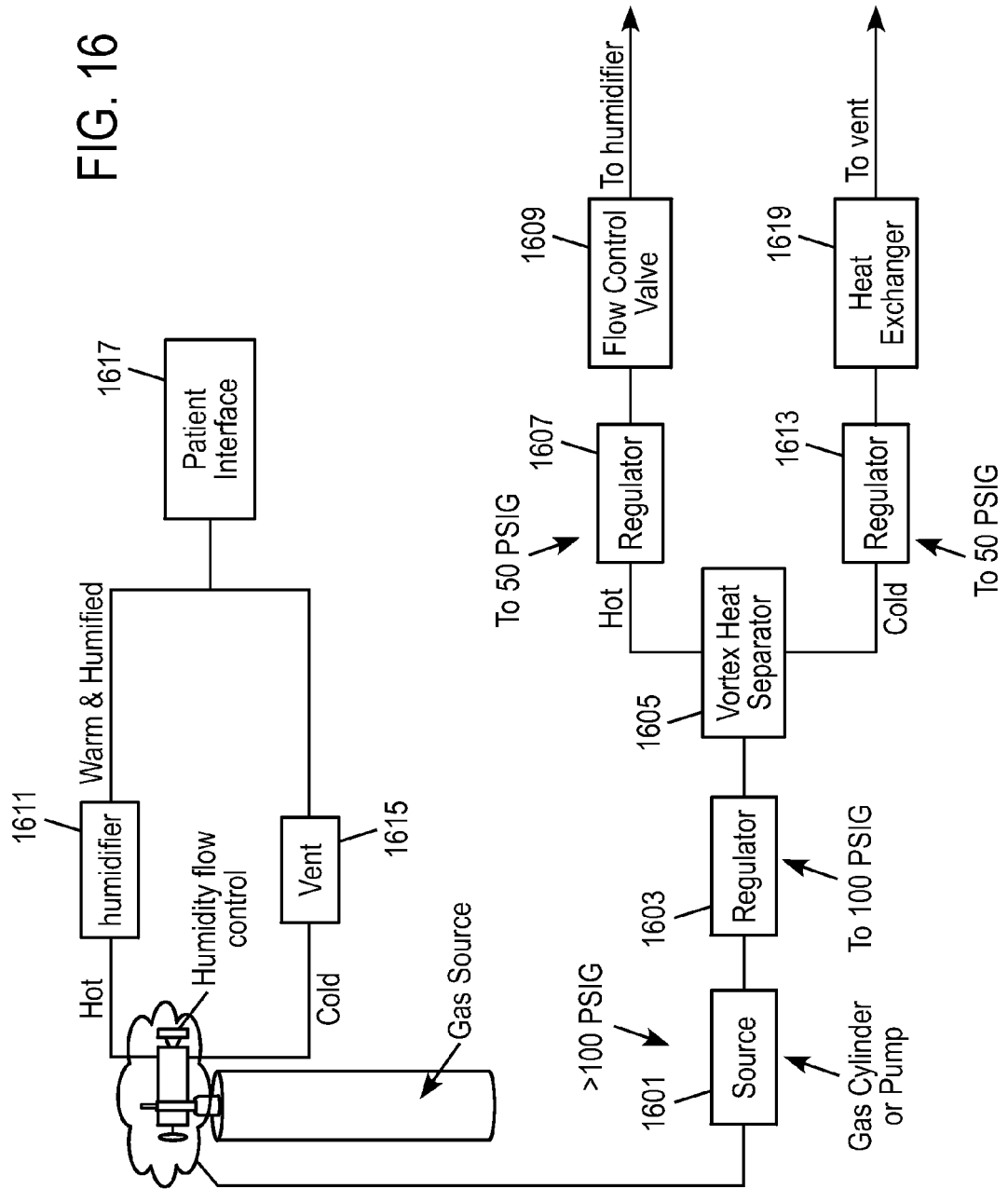
FIG. 16 shows a system for heated humidified gas, according to an exemplary embodiment.

FIG. 16 shows a system for heated humidified gas. A source 1601, such as a gas cylinder or pump, may provide gas at approximately 100 psig or more. The source 1601 may provide gas to a regulator 1603 that regulates gas pressure to a predetermined and/or desired level. In certain embodiments, this may be approximately 100 psig. The gas is then provided to a vortex heat separator 1605, where hot gas may be provided to a second regulator 1607, where the gas pressure is regulated to a predetermined and/or desired level. In certain embodiments, this may be approximately 50 psig. A flow control valve 1609 may then provide the hot gas to a humidifier 1611. From the vortex heat separator 1605, cold gas may be provided to a third regulator 1613, where the gas pressure is regulated to a predetermined and/or desired level. The third regulator 1613 may provide the cold gas to a heat exchanger 1619. In certain embodiments, this may be approximately 50 psig. The cold gas may be provided to a ventilator 1615. Warm and humidified gas from the humidifier may be combined with the cold gas from the ventilator prior to, within or separate from a patient interface 1617.

Figure 17:
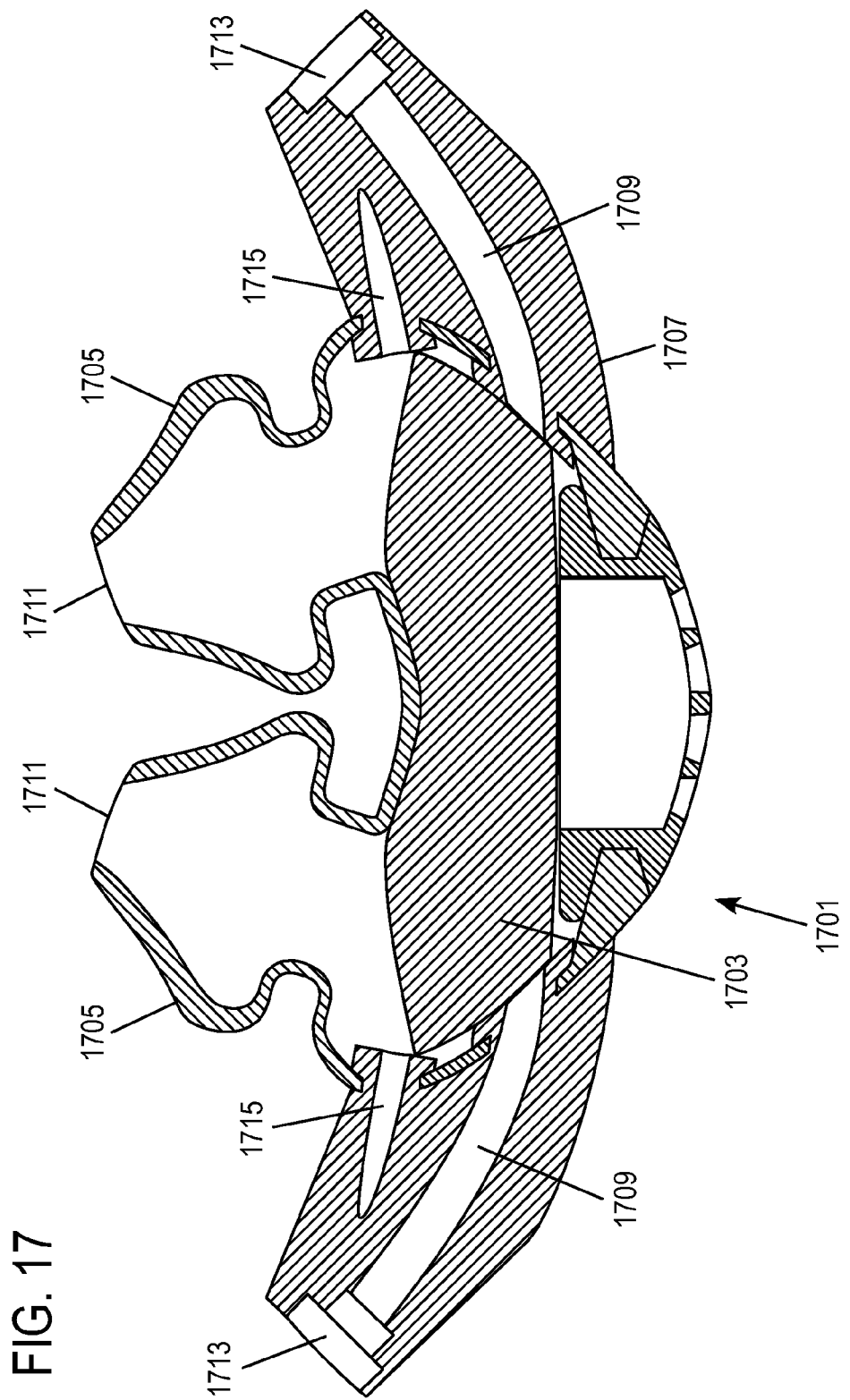
FIG. 17 shows a nasal interface with a hygroscopic material incorporated therein, according to an exemplary embodiment.

FIG. 17 shows a nasal interface 1701 with a hygroscopic material 1703 incorporated therein. Hygroscopic material captures the heat and moisture from a patient's exhaled breaths and returns the heat and moisture to the patient's inspired gas. It is a passive technology that requires no further complicating factors such as electricity and moisture feed to establish a heat/humidification target for a patient, thereby providing a simple implementation of a heat/moisture system for ventilation. Examples of suitable hygroscopic materials include commercially available heat and moisture exchangers (HME), and hygroscopically treated heat and moisture exchangers (HHME) such as paper or polypropylene inserts treated with hygroscopic chemicals, usually calcium or lithium chloride, to enhance moisture retention. The hygroscopic material 1703 may be porous. In certain embodiments, all or nearly all of the patient's inspired and/or expired gas may pass through the hygroscopic material 1703. In these embodiments, nasal pillows 1705 may seal the patient's nose. Preferably all the flow exhaled by the patient and all the flow inhaled by the patient should pass through the hygroscopic material to optimize heat and moisture retention during the expiration phase and maximize the heating and humidification of the breathable gas inhaled by the patient. Optimal sizes are generally dependent upon the material used, its thickness and the fluid-dynamic design of the patient interface. A preferred embodiment may have most of the surface of the hygroscopic element exposed to the flow exhaled and inhaled by the patient, and may have a thickness of preferably about 2 to about 20 mm and a surface area of about 150 to about 800 mm$^2$.

Embodiments of the present invention integrate hygroscopic material within a nasal interface to provide a patient interface that heats and humidifies the patient gas. The hygroscopic material 1703 may be located anywhere in a gas flow path within the nasal interface 1701. In a preferred embodiment, the hygroscopic material 1703 may be located within a pillows portion 1705 of the nasal interface 1701 or within cushions attached to the pillows portion 1705. The pillows portion 1705 may extend into and/or contact the nose of a patient, and may extend into a manifold portion 1707 of the nasal interface. One or more channels 1709 may provide a gas flow path through the nasal interface 1701 from inputs 1713 from a patient delivery circuit to outlets 1711 near or in the patient's nose. One or more sensing ports 1715 may detect pressure, humidity or other variables. Preferably, the one or more sensing ports 1715 are located on a patient side of the hygroscopic material 1703 to produce more accurate readings.

The hygroscopic element can be used in conjunction with any of the previously disclosed active humidification systems to minimize the amount of water required by the ventilation system. Whenever a hygroscopic element is present, the delivery of humidification can be timed to the breathing cycle of the patient and the delivery of active humidification can be decreased or even suspended during certain phases of the breathing cycle, such as during exhalation. This may allow for optimal humidification of the patient ensuring minimal use of water and energy, thus increasing the portability of the ventilation device.

A location within the pillows portion 1705 may provide several advantages:

(1) By incorporating the hygroscopic material 1703 in direct proximity to the patient's nose, there a maximized efficiency because of the negligible heat loss between the hygroscopic material and the patient.

(2) Both the hygroscopic material 1703 and the pillows interface 1705 may be made from compliant materials, and therefore co-locating these materials provides the smallest possible implementation of the patient interface without sacrificing function of either material.

(3) Both the pillows interface 1705 and the hygroscopic material 1703 may be user-exchangeable components that are periodically changed to maintain system performance and cleanliness. Therefore, co-locating the pillows 1705 and hygroscopic materials 1703 may provide for the simplest user maintenance experience.

(4) The location of the hygroscopic material 1703 may minimize sound for at the patient gas entry point. Sound may propagate through both the air and the patient. The hygroscopic material 1703 acts to diffuse gas flow prior to the ventilation gas entering the patient, and, therefore, reducing the noise levels of the gas flow. Additionally, the hygroscopic material 1703 may diffuse gas flow exhaled by the patient to the ambient and or the gas flow vented to the ambient from the patient interface therefore, reducing the noise.

One or more controllers may regulate the systems and methods of the present invention. The one or more controls may include one or more processors and one or more memories. The one or more controls may control the ventilator and/or the humidification systems. The one or more controls may receive signals from one or more sensors and process those signals to create a new signal to send to the ventilator and/or humidifier to adjust gas delivery parameters.

Although the foregoing description is directed to the preferred embodiments of the invention, it is noted that other variations and modifications will be apparent to those skilled in the art, and may be made departing from the spirit or scope of the invention. Moreover, features described in connection with one embodiment of the invention may be used in conjunction with other embodiments, even if not explicitly stated above. The present invention may be embodied in other specific forms without departing from its spirit or essential characteristics. The described embodiments are to be considered in all respects only as illustrative and not restrictive.

The invention claimed is:

1. A nasal interface apparatus for receiving ventilation gas from gas delivery tubing and for humidifying ventilation gas, the nasal interface apparatus comprising:
   one or more channels within the nasal interface apparatus to deliver gas from a gas delivery circuit to one or more structures, wherein the one or more structures are in fluid communication with the one or more channels to direct ventilation gas to a patient's nose; and
   a hygroscopic material within the nasal interface apparatus extending across an entirety of a cross sectional area of a flow path of the ventilation gas and defined by one or more channel interface sides each facing a respective one of the one or more channels within the nasal interface, a patient interface side facing the one or more structures, and an exhalation side, the channel interface sides being angularly offset from the exhalation side and the patient interface side;
   wherein substantially all inhaled ventilation gas and all exhaled gas is diffused through the hygroscopic material.

2. The nasal interface apparatus of claim 1, wherein the one or more structures are one or more nasal pillows, and wherein the hygroscopic material is located within the one or more nasal pillows or within a cushion attached to the one or more nasal pillows.

3. The nasal interface apparatus of claim 1, further comprising at least one pressure sensor device.

4. The nasal interface apparatus of claim 3, wherein the at least one pressure sensor is located on a patient side of the hygroscopic material.

5. The nasal interface apparatus of claim 1, wherein the gas delivery circuit has an inside diameter of approximately 2-14 mm.

6. The nasal interface apparatus of claim 1, wherein the nasal interface apparatus is used with a portable ventilation system.

7. The nasal interface apparatus of claim 1, wherein delivery of the humidified ventilation gas is servo controlled.

8. The nasal interface apparatus of claim 7, wherein the servo controls humidification levels based on the patient's need.

9. The nasal interface apparatus of claim 7, wherein the servo predictively controls humidification levels.

10. The nasal interface apparatus of claim 9, wherein the servo considers gas flow delivered to the patient, ambient temperatures, ambient humidity, and combinations thereof.

11. The nasal interface apparatus of claim 1, wherein the humidified ventilation gas is delivered in synchrony with the patient's breathing cycle.

12. The nasal interface apparatus of claim 11, wherein more humidified ventilation gas is delivered during the patient's inspiratory phase than during the patient's expiratory phase.

13. The nasal interface apparatus of claim 1, further comprising heated tubing.

14. The nasal interface apparatus of claim 13, wherein energy is applied to the heated tubing in synchrony with the patient's need and the patient's breathing cycle.

15. A method for delivering humidified ventilation gas, the method comprising:
    providing a nasal interface comprising:
        one or more channels within the nasal interface to deliver gas from a gas delivery circuit to one or more structures, wherein the one or more structures are in fluid communication with the one or more channels to direct ventilation gas to a patient's nose; and
        a hygroscopic material within the nasal interface apparatus extending across an entirety of a cross sectional area of a flow path of the ventilation gas and defined by one or more channel interface sides each facing a respective one of the one or more channels within the nasal interface, a patient interface side facing the one or more structures, and an exhalation side, the channel interface sides being angularly offset from the exhalation side and the patient interface side;
        wherein substantially all inhaled ventilation gas and all exhaled gas is diffused through the hygroscopic material; and
    delivering humidified ventilation gas to the patient.

16. The method of claim 15, wherein the one or more structures are one or more nasal pillows, and wherein the hygroscopic material is located within the one or more nasal pillows or within a cushion attached to the one or more nasal pillows.

17. The method of claim 15, further comprising at least one pressure sensor, wherein the at least one pressure sensor is located on a patient side of the hygroscopic material.

18. The method of claim 15, wherein the gas delivery circuit has an inside diameter of approximately 2-14 mm.

19. The method of claim 15, further comprising controlling delivery of the humidified ventilation gas with a servo.

20. The method of claim 15, further comprising delivering the humidified ventilation gas in synchrony with the patient's breathing cycle.

* * * * *